United States Patent
Robles et al.

[11] Patent Number: 6,004,306
[45] Date of Patent: *Dec. 21, 1999

[54] ABSORBENT ARTICLE WITH MULTI-DIRECTIONAL EXTENSIBLE SIDE PANELS

[75] Inventors: Miguel Alvaro Robles; Kimberly Ann Dreier, both of Cincinnati; Carl Louis Bergman, Loveland; Donald Carroll Roe, West Chester; Constance Lee Dakin, Cincinnati, all of Ohio

[73] Assignee: The Procter & Gamble company, Cincinnati, Ohio

[*] Notice: This patent is subject to a terminal disclaimer.

[21] Appl. No.: 08/915,471

[22] Filed: Aug. 20, 1997

Related U.S. Application Data

[63] Continuation of application No. 08/155,048, Nov. 19, 1993, abandoned.

[51] Int. Cl.⁶ .................................................. A61F 13/18
[52] U.S. Cl. ........................ 604/385.1; 604/386; 604/394
[58] Field of Search ................................ 604/385.1–402; 2/400–408; 602/68–73

[56] References Cited

U.S. PATENT DOCUMENTS

| | | | |
|---|---|---|---|
| 2,743,725 | 5/1956 | Matthews | 604/392 |
| 3,800,796 | 4/1974 | Jacob . | |
| 3,860,003 | 1/1975 | Buell . | |
| 3,867,946 | 2/1975 | Mesek et al. | 604/390 |
| 4,010,754 | 3/1977 | Pieniak | 604/390 |
| 4,055,182 | 10/1977 | Mack | 604/390 |
| 4,090,516 | 5/1978 | Schaar . | |
| 4,209,016 | 6/1980 | Schaar . | |

(List continued on next page.)

FOREIGN PATENT DOCUMENTS

| | | |
|---|---|---|
| 0 487 921 A2 | 6/1992 | European Pat. Off. . |
| 0 547 497 A2 | 6/1993 | European Pat. Off. . |
| 418181 | 3/1974 | U.S.S.R. ........................ 604/394 |
| 2 080 093 | 2/1982 | United Kingdom . |
| WO 92/07531 | 5/1992 | WIPO . |
| WO-A-95/13775 | 5/1995 | WIPO . |
| WO 96/21412 | 7/1996 | WIPO . |
| WO 96/29038 | 9/1996 | WIPO . |
| WO-A-96/35402 | 11/1996 | WIPO . |

OTHER PUBLICATIONS

Translation of Japanese 47428/1992.
Translation of Japanese 58610/1989.
Translation of JP 2,682,969.

Primary Examiner—John G. Weiss
Assistant Examiner—K. M. Reichle
Attorney, Agent, or Firm—David M. Weirich; Michael S. Kolodesh; Jacobus C. Rasser

[57] ABSTRACT

Absorbent articles such as disposable diapers, incontinent briefs, diaper holders, training pants, feminine hygiene garments, and the like, having extensible side panel features that improve the dynamic fit of the diaper around the legs and waist of the wearer. Such absorbent articles include a containment assembly including a liquid pervious topsheet; a liquid impervious backsheet; an absorbent core disposed between the topsheet and the backsheet; and extensible side panels, each including a waist panel and a thigh panel disposed along each longitudinal edge of the containment assembly in the first waist region. The waist panel and the thigh panel are operatively associated so that the waist panel has a primary direction of extensibility in one direction and the thigh panel has a primary direction of extensibility in a different direction. This forms a multi-directional extensible side panel wherein the waist panel provides tension around the wearer's waist to maintain fit about the waist and to hold the diaper on the wearer, and the thigh panel expands and contracts to maintain a dynamic fit around the leg of the wearer. Thus, the waist and thigh panels reduce the negative effects of the dynamic forces on the absorbent article, such as sagging and gapping that can cause leakage, while increasing freedom of motion and wearer comfort.

16 Claims, 10 Drawing Sheets

U.S. PATENT DOCUMENTS

| | | | |
|---|---|---|---|
| 4,229,835 | 10/1980 | Shaw | 604/385.2 |
| 4,338,938 | 7/1982 | Seavitt | 604/377 |
| 4,355,425 | 10/1982 | Jones et al. | |
| 4,381,781 | 5/1983 | Sciaraffa et al. | |
| 4,397,646 | 8/1983 | Daniels | 604/385.2 |
| 4,500,316 | 2/1985 | Damico | 604/389 |
| 4,515,595 | 5/1985 | Kievit et al. | |
| 4,568,344 | 2/1986 | Suzuki et al. | 604/389 |
| 4,585,447 | 4/1986 | Karami | 604/385 |
| 4,680,030 | 7/1987 | Coates et al. | |
| 4,704,115 | 11/1987 | Buell. | |
| 4,756,709 | 7/1988 | Stevens. | |
| 4,826,499 | 5/1989 | Ahr. | |
| 4,850,988 | 7/1989 | Aledo et al. | |
| 4,857,067 | 8/1989 | Wood et al. | |
| 4,861,652 | 8/1989 | Lippert et al. | |
| 4,911,702 | 3/1990 | O'Leary et al. | |
| 4,932,950 | 6/1990 | Johnson | 604/392 |
| 4,937,887 | 7/1990 | Schreiner. | |
| 4,938,753 | 7/1990 | Van Gompel et al. | |
| 4,938,757 | 7/1990 | Van Gompel et al. | |
| 4,940,464 | 7/1990 | Van Gompel et al. | |
| 4,998,929 | 3/1991 | Bjorksund et al. | 604/385.2 |
| 5,055,103 | 10/1991 | Nomura et al. | |
| 5,080,741 | 1/1992 | Nomura et al. | |
| 5,092,861 | 3/1992 | Nomura et al. | |
| 5,143,679 | 9/1992 | Weber et al. | |
| 5,151,092 | 9/1992 | Buell et al. | |
| 5,167,897 | 12/1992 | Weber et al. | |
| 5,196,000 | 3/1993 | Clear et al. | |
| 5,242,436 | 9/1993 | Weil et al. | |
| 5,246,433 | 9/1993 | Hasse et al. | 604/396 |
| 5,358,500 | 10/1994 | Lavon et al. | 604/385.2 |
| 5,368,584 | 11/1994 | Clear et al. | 604/385.2 |
| 5,370,634 | 12/1994 | Ando et al. | 604/385.1 |
| 5,383,871 | 1/1995 | Carlin et al. | 604/386 |
| 5,554,145 | 9/1996 | Roe et al. | 604/358 |
| 5,669,897 | 9/1997 | Lavon et al. | 604/385.2 |

ABSORBENT ARTICLE WITH MULTI-DIRECTIONAL EXTENSIBLE SIDE PANELS

This application is continuation of application Ser. No. 08/155,048, filed on Nov. 19, 1993, which is abandoned.

FIELD OF INVENTION

The present invention relates to absorbent articles such as diapers, incontinent briefs, diaper holders, training pants, and the like and, more particularly, to absorbent articles having extensible side panels providing dynamic fit about the wearer as well as improved comfort characteristics.

BACKGROUND OF THE INVENTION

Infants and other incontinent individuals wear absorbent articles such as diapers to receive and contain urine and other body exudates. Absorbent articles function both to contain discharged materials and to isolate these materials from the body of the wearer and from the wearer's garments and bed clothing. Disposable absorbent articles having many different basic designs are known to the art. For example, U.S. Pat. No. Re. 26,152, entitled "Disposable Diaper" issued to Duncan and Baker on Jan. 31, 1967 describes a disposable diaper which has achieved wide acceptance and commercial success.

In order to provide better fit and to reduce leakage, absorbent articles have been provided with elastic features. U.S. Pat. No. 3,860,003, entitled "Contractible Side Portions For Disposable Diaper", issued to Kenneth B. Buell on Jan. 14, 1975, describes an elasticized leg cuff disposable diaper which has achieved wide acceptance and commercial success. U.S. Pat. No. 5,151,092 issued to Buell et al., on Sep. 29, 1992 describes an absorbent article having an elastic waist feature improving dynamic fit as well as containment characteristics. U.S. Pat. No. 4,857,067 issued to Wood, et al. on Aug. 15, 1989 describes a disposable diaper with elastic side panels to fit over the hips of the wearer. The elastic features are designed to expand and contract with the wearer's motions and to maintain the fit of the absorbent article about the wearer during use (i.e. provide sustained dynamic fit).

However, it has been found that absorbent articles having elastic features still have a tendency to gap or to be too tight during use. As the wearer moves, changes occur in the wearer's body measurements, particularly in the hips and thighs, thereby subjecting the diaper to dynamic forces. These dynamic forces tend to deform the materials making up the diaper and tend to push the diaper away from the body. As a result, the diaper tends to sag or gap away from the wearer, especially in the regions of dynamic motion such as the hips and thighs. Conventional disposable diapers were originally made of non-elastic materials unable to elastically expand to accommodate the wearer's bodily movements. The introduction of unitary elastic side panel features to conventional disposable diapers has improved their fit and comfort by allowing the side panels to expand generally in the lateral direction around the waist of the wearer. However, unitary elastic side panels are unable to fully elastically expand in directions other than the lateral direction without placing undue pressure on the wearer's legs, hips or waist. Because the wearer's movements create dynamic forces in many different directions, conventional disposable diapers having unitary elastic side panel features still tend to gap away from the body causing an increased likelihood of leakage and exerting forces on the wearer that can be uncomfortable and cause red marks on the wearer's skin.

Thus, it would be advantageous to provide an absorbent article having improved extensible side panels that provide better fit and wearer comfort as well as reduced leakage, sagging and gapping during use.

Therefore, it is an object of the present invention to provide an absorbent article having improved dynamic fit about the waist and leg of the wearer by reducing sagging and gapping of the absorbent article on the wearer.

It is a further object of the present invention to provide an absorbent article having unique multi-directional extensible side panels that expand and contract in multiple directions to minimize the effects of the dynamic forces created by the wearer's movements, thereby increasing freedom of motion and comfort for the wearer while improving sustained dynamic fit of the absorbent article.

These and other objectives of the present invention will be more readily apparent when considered in reference to the following description and when taken in conjunction with the accompanying drawings.

SUMMARY OF THE INVENTION

The present invention provides absorbent articles such as disposable diapers, incontinence briefs, diaper holders, training pants, feminine hygiene garments, and the like, having extensible side panel features that improve the dynamic fit of the diaper around the legs and waist of the wearer. Such absorbent articles comprise a containment assembly comprising a liquid pervious topsheet; a liquid impervious backsheet; an absorbent core disposed between the topsheet and the backsheet; and extensible side panels, each comprising a waist panel and a thigh panel disposed along each longitudinal edge of the containment assembly in the first waist region. The waist panel and the thigh panel are preferably operatively associated so that the waist panel has a primary direction of extensibility in one direction and the thigh panel has a primary direction of extensibility in a different direction. This forms a multi-directional extensible side panel wherein the waist panel provides tension around the wearer's waist to maintain fit about the waist and to hold the diaper on the wearer, and the thigh panel expands and contracts to maintain a dynamic fit around the leg of the wearer. Thus, the waist and thigh panels reduce the negative effects of the dynamic forces on the absorbent article, such as sagging and gapping that can cause leakage, while increasing freedom of motion and wearer comfort.

The extensible side panels may comprise a single piece of extensible material or two or more separate elements joined together to form the extensible side panels. Further, the extensible side panels may be extensions of other elements of the absorbent article or a separate structure joined to another element of the absorbent article. Mechanical operations such as pleating, corrugating, ring-rolling or the like can be performed on the side panels to provide the unique multi-directional extensibility characteristics of the present invention. Alternatively, the material may be folded, slit or cut to form distinct waist and thigh panels having different directions of extensibility.

In yet other embodiments, the multi-directional stretch characteristics are derived from extensible side panels comprising separate waist and thigh panel members having nonparallel primary directions of extensibility. In a preferred embodiment, the waist panel has a primary direction of extensibility about the waist of the wearer and the thigh panel has a primary direction of extensibility that is nonparallel to that of the waist panel, preferably at an angle to the lateral and longitudinal directions. In this configuration, the waist panel elastically contracts to provide an inward force that holds the absorbent article in place about the wearer during use while the thigh panel expands and contracts in conjunction with the leg movements of the wearer. Thus, the multi-directional extensible side panels reduce the possibility of gapping in the waist and thigh regions of the absorbent article as well as reduce the likelihood of marks on the wearer's skin resulting from tension and dynamic forces.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements and in which:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A preferred embodiment of an absorbent article of the present invention is the disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, training pants, and the like.

Figure 1:
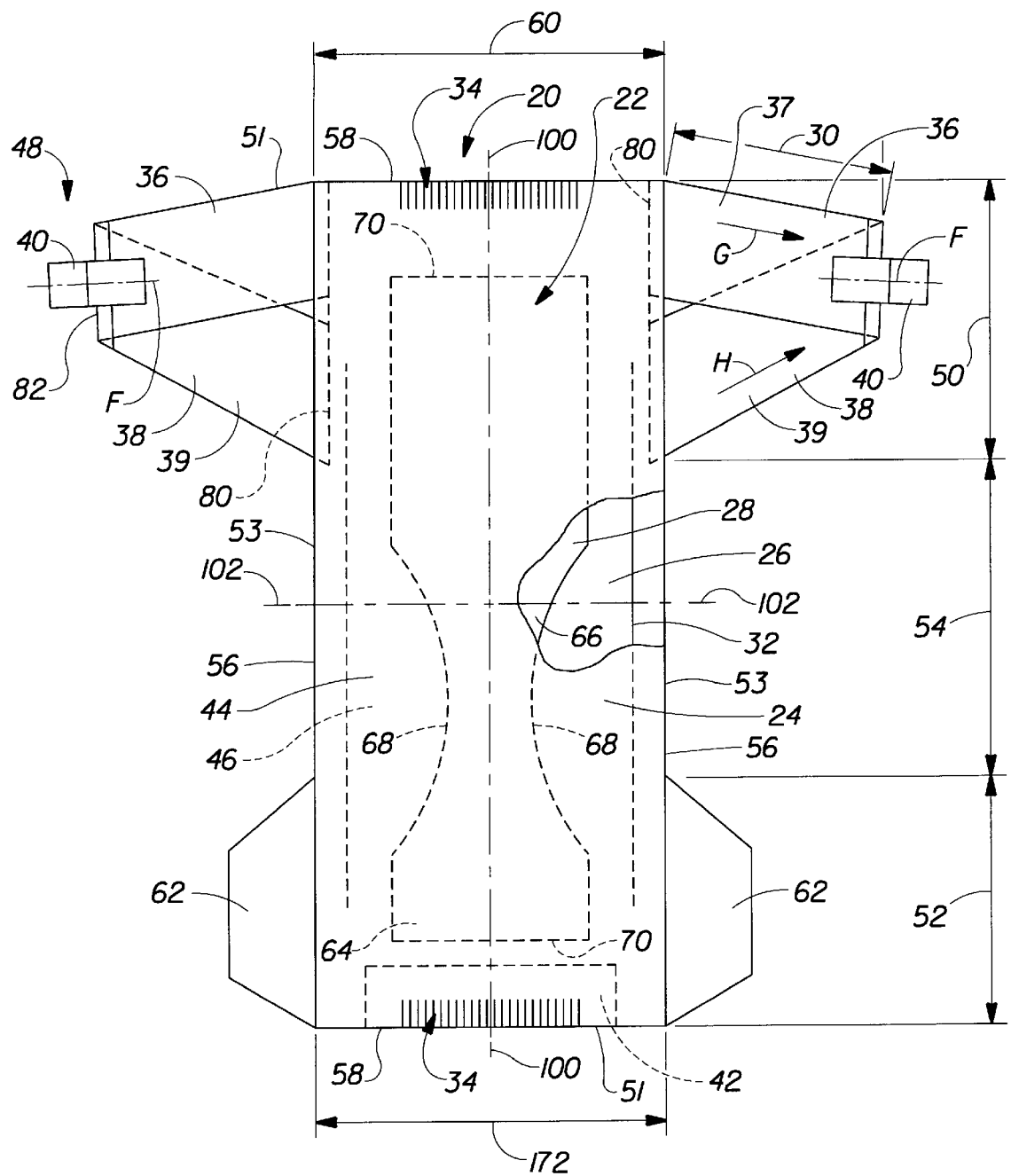
FIG. 1 is a plan view of a disposable diaper embodiment of the present invention having portions cut away to reveal underlying structure, the inner surface of the diaper facing the viewer.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 preferably comprises a containment assembly 22 comprising a liquid pervious topsheet 24; a liquid impervious backsheet 26 joined with the topsheet 24; and an absorbent core 28 positioned between the topsheet 24 and the backsheet 26. The diaper further comprises elasticized leg cuffs 32; ear flaps 62; an elastic waist feature 34; a fastening system 48 comprising a pair of first fastening members 40, each having a primary centerline F, and a second fastening member 42; and extensible side panels 30, each comprising an extensible waist panel 36 and a thigh panel 38. Each extensible side panel 30 has a proximal edge 80 and a distal edge 82.

The diaper 20 also has two centerlines, a longitudinal centerline 100 and a transverse centerline 102. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

As shown in FIG. 1, the extensible side panel 30 preferably comprises a waist panel 36 and a thigh panel 38 that are operatively associated in a contractible condition such that the waist panel 36 and the thigh panel 38 have nonparallel primary directions of extensibility. (The terms "waist panel" and "thigh panel" refer to extensible components of the extensible side panels, each having a primary direction of extensibility. As used herein, "primary direction of extensibility" refers to the direction in which an extensible member has the greatest extension). FIG. 1 shows a preferred embodiment of the present invention wherein the waist panel 36 has a primary direction of extensibility about the waist of the wearer and the thigh panel 38 has a primary direction of extensibility nonparallel to that of the waist panel 36. (The primary direction of extensibility in the waist panel 36 is represented by arrow G in FIG. 1. The primary direction of extensibility in the thigh panel 38 is represented by arrow H in FIG. 1.) In an especially preferred embodiment, the thigh panel 38 has a primary direction of extensibility that is nonparallel to the lateral or the longitudinal direction. (The lateral direction is defined as the direction parallel to the lateral centerline of the diaper, and the longitudinal direction is defined as the direction parallel to the longitudinal centerline.) The extensible side panels 30 provide a more comfortable and contouring fit by initially conformably fitting the diaper 20 to the wearer and sustaining the fit throughout the time of wear well past when the diaper 20 has been loaded with exudates since the extensible side panels 30 allow the sides of the diaper 20 to expand and contract. The waist panel 36 elastically contracts providing an inward force that holds the diaper in place about the wearer during use. The thigh panel 38 expands and contracts with the leg movements of the wearer. Thus, the multi-directional extensible waist and thigh panels reduce the possibility of gapping in the waist or thigh regions of the diaper and the likelihood of marks on the wearer resulting from fastening tension and dynamic forces.

The diaper 20 is shown in FIG. 1 to have an inner surface 44 (facing the viewer in FIG. 1), an outer surface 46 opposed to the inner surface 44, a first waist region 50, a second waist region 52 opposed to the first waist region 50, a crotch region 54 positioned between the first waist region 50 and the second waist region 52, a waist encirclable edge 51, a leg encirclable edge 53. The longitudinal edges 56 of the containment assembly 22 form a portion of the leg encirclable edge 53 and the end edges 58 of the containment assembly 22 form a portion of the waist encirclable edge 51. The inner surface 44 of the diaper 20 comprises that portion of the diaper 20 which is positioned adjacent to the wearer's body during use (i.e., the inner surface 44 generally is formed by at least a portion of the topsheet 24 and other components joined to the topsheet 24). The outer surface 46 comprises that portion of the diaper 20 which is positioned away from the wearer's body (i.e., the outer surface 46 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The first waist region 50 and the second waist region 52 extend from the end edges 58 to the crotch region 54. The first waist region 50 comprises a central region 60 and a pair of extensible side panels 30 which typically comprise the outer lateral portions of the first waist region 50. The second waist region 52 comprises a central region 172 and a pair of ear flaps 62 which typically comprise the outer lateral portions of the second waist region 52. The extensible side panels positioned in the first waist region 50 are designated 30 while the ear flaps in the second waist region 52 are designated 62.

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly 22 generally comprises the holder and the liner (i.e., the containment assembly 22 comprises one or more layers of material to define the holder while the liner comprises an absorbent composite such as a topsheet, a backsheet, and an absorbent core.) Generally, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

FIG. 1 shows a preferred embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28. While the topsheet 24, the backsheet 26, and the absorbent core 28 may be assembled in a variety of well known configurations, preferred containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992; each of which is incorporated herein by reference.

Figure 2:
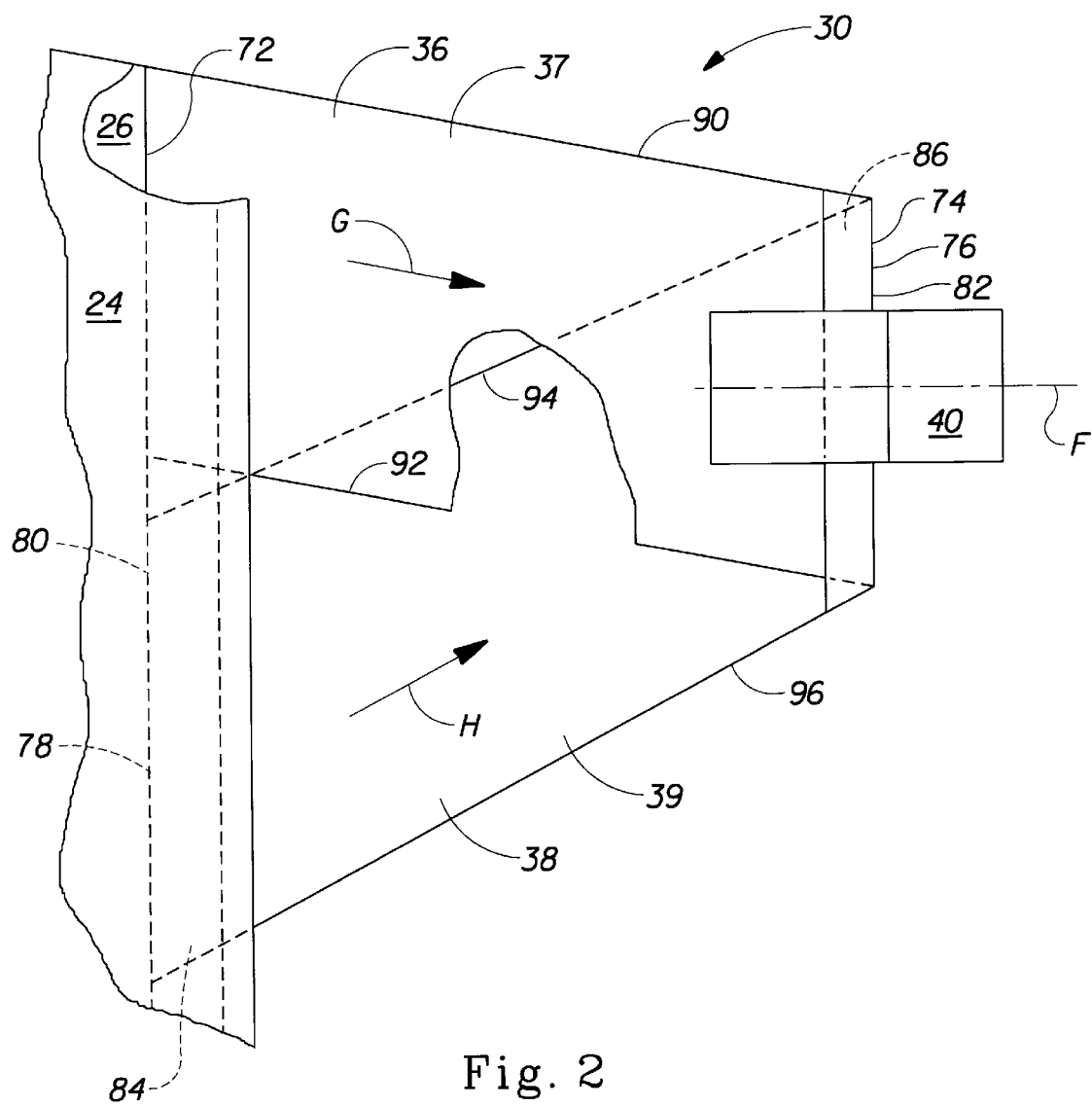
FIG. 2 is an enlarged, fragmentary view of the inner surface of one version of the extensible side panel of the diaper shown in FIG. 1 having portions cut away to reveal the underlying structure.
Figure 3:
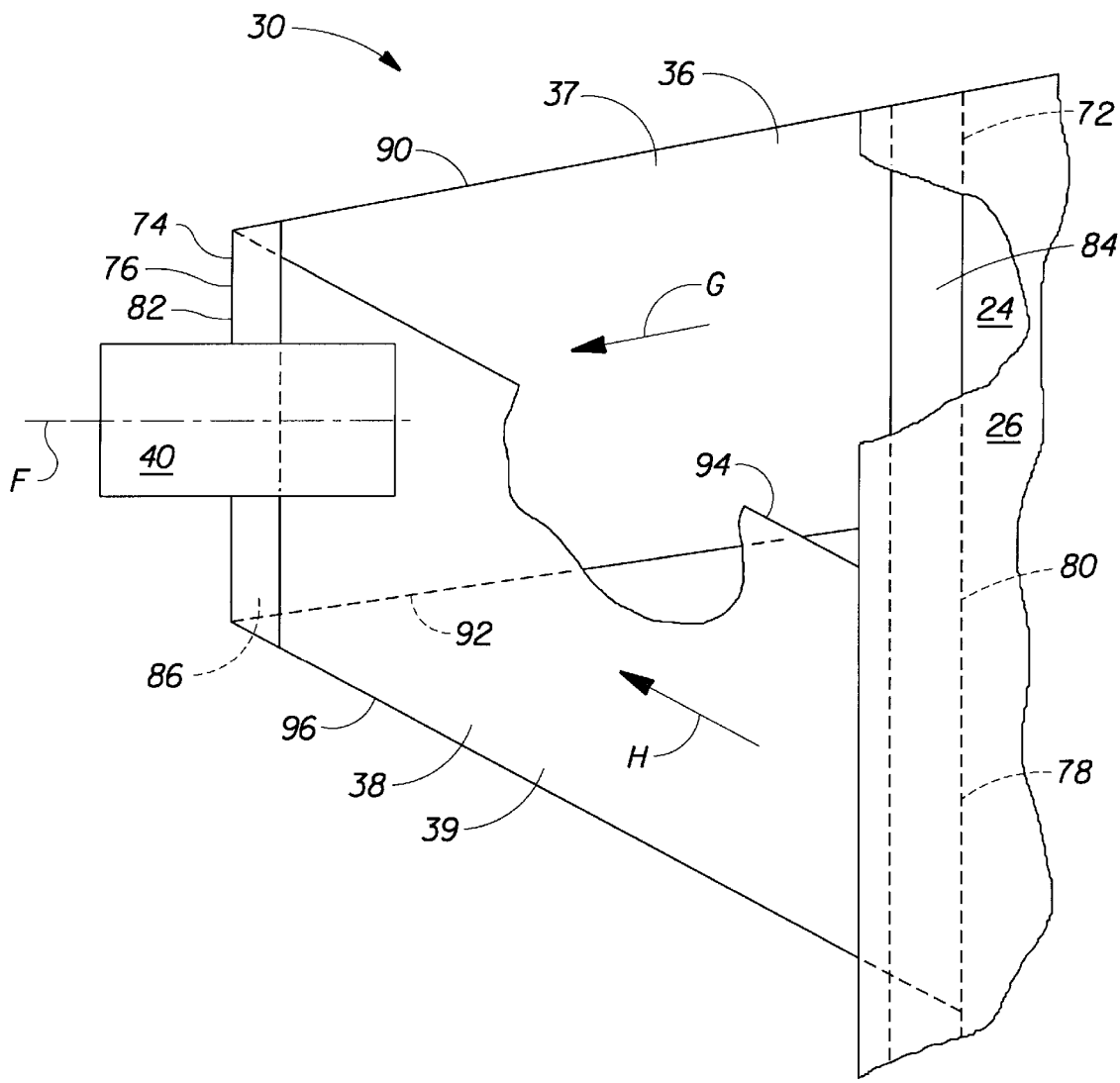
FIG. 3 is an enlarged, fragmentary view of the outer surface of one version of the extensible side panel of the diaper shown in FIG. 1 having portions cut away to reveal the underlying structure.

FIGS. 2 and 3 are enlarged, fragmentary views of the extensible side panel 30 having portions cut away to reveal the underlying structure. FIG. 2 shows the inner surface of the extensible side panel 30 and FIG. 3 shows the outer surface of the extensible side panel 30. In the multiple component embodiment shown in FIGS. 2 and 3, the extensible side panel 30 comprises a waist panel 36 having a waist panel proximal edge 72, a waist panel distal edge 74, a waist panel first lateral edge 90, and a waist panel second lateral edge 92, and a thigh panel 38 having a thigh panel proximal edge 78, a thigh panel distal edge 76, a thigh panel first lateral edge 94, and a thigh panel second lateral edge 96. As shown in FIG. 2, the waist panel proximal edge 72 and the thigh panel proximal edge 78 may be joined between the topsheet 24 and the backsheet 26. Alternatively, either the waist panel proximal edge 72 or the thigh panel proximal edge 78, or both, can both be joined to the outer surface 46 of the backsheet 26, the inner surface 44 of the topsheet 24. FIG. 2 additionally shows the waist panel 36 and the thigh panel 38 operatively associated in a partially overlapping configuration wherein the waist panel distal edge 74 is joined to the thigh panel distal edge 76.

As shown in FIG. 2, a first fastening member 40 is preferably disposed adjacent the distal edge 82 of the extensible side panel 30. The first fastening member 40 is preferably operatively associated such that it is joined to both the waist panel 36 and the thigh panel 38. Thus, a force on the first fastening member 40 provides tension throughout both the waist panel 36 and the thigh panel 38. FIG. 2 also shows a proximal stiffening member 84 disposed adjacent the proximal edge 80 of the extensible side panel 30 and a distal stiffening member 86 disposed adjacent the distal edge 82 of the extensible side panel 30. The proximal stiffening member 84 prevents the proximal edge 80 of each extensible side panel 30 from buckling while in use and the distal stiffening member 86 helps to distribute the forces on the fastening system 48 throughout each extensible side panel 30. As shown in FIG. 2, the proximal stiffening member 84 and the distal stiffening member 86 may be separate elements joined to the absorbent article by attachment means (not shown) such as those well known in the art, or may be unitary with an element of the absorbent article.

The absorbent core 28 may be any absorbent member which is generally compressible, conformable, non-irritating to the wearer's skin, and capable of absorbing and retaining liquids such as urine and other certain body exudates. As shown in FIG. 1, the absorbent core 28 has an outer surface 64, an inner surface 66, side edges 68, and waist edges 70.

The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20. The size and absorbent capacity of the absorbent core 28 may also be varied to accommodate wearers ranging from infants through adults.

One embodiment of the diaper 20 has asymmetric, modified T-shaped, absorbent core 28 having ears in the first waist region but a generally rectangular shape in the second waist region. Exemplary absorbent structures for use as the absorbent core 28 of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing acquisition/distribution core of chemically stiffened fibers positioned over the absorbent storage cores as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The backsheet 26 is positioned adjacent the outer surface 64 of the absorbent core 28 and is preferably joined thereto by attachment means (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the diaper 20 such as bedsheets and undergarments. Further, the backsheet 26 may permit vapors to escape from the absorbent core 28 (i.e., breathable) while still preventing exudates from passing through the backsheet 26. Thus, the backsheet 26 may comprise a woven or nonwoven material, polymeric films such as thermoplastic films of polyethylene or polypropylene, or composite materials such as a film-coated nonwoven material. An example of a suitable backsheet is a thermoplastic film having a thickness of from about 0.012 mm (0.5 mil) to about 0.051 mm (2.0 mils). Other suitable materials for the backsheet 26 include RR8220 blown films and RR5475 cast films as manufactured by Tredegar Industries, Inc. of Terre Haute, Ind. The backsheet 26 is preferably embossed and/or matte finished to provide a more clothlike appearance.

The topsheet 24 is positioned adjacent the inner surface 66 of the absorbent core 28 and is preferably joined thereto and to the backsheet 26 by attachment means (not shown) such as those well known in the art. Suitable attachment means are described with respect to joining the backsheet 26 to the absorbent core 28. In a preferred embodiment of the present invention, the topsheet 24 and the backsheet 26 are joined directly to each other in the diaper periphery 55 and are indirectly joined together by directly joining them to the absorbent core 28 by the attachment means (not shown).

The topsheet 24 is compliant, soft feeling, and non-irritating to the wearer's skin. Further, the topsheet 24 is preferably liquid pervious permitting liquids (e.g., urine) to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is preferably made of a hydrophobic material to isolate the wearer's skin from liquids which have passed through the topsheet 24 and are contained in the absorbent core 28 (i.e. to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S.

Pat. No. 4,988,345 entitled "Absorbent Articles with Rapid Acquiring Absorbent Cores" issued to Reising on Jan. 29, 1991, each of which is incorporated by reference herein.

There are a number of manufacturing techniques which may be used to manufacture the topsheet 24. For example, the topsheet 24 may be a nonwoven web of fibers. When the topsheet 24 comprises a nonwoven web, the web may be spunbonded, carded, wet-laid, melt-blown, hydroentangled, combinations of the above, or the like. A suitable topsheet 24 is carded and thermally bonded by means well known to those skilled in the fabrics art. A satisfactory topsheet 24 comprises staple length polypropylene fibers having a denier of about 2.2. As used herein, the term "staple length fibers" refers to those fibers having a length of at least about 15.9 mm (0.625 inches). Preferably, the topsheet 24 has a basis weight from about 18 to about 25 grams per square meter. A suitable topsheet is manufactured by Veratec, Inc., a Division of International Paper Company, of Walpole, Mass. under the designation P-8.

The diaper 20 preferably further comprises elasticized leg cuffs 32 for providing improved containment of liquids and other body exudates. Each elasticized leg cuff 32 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff. While each elasticized leg cuff 32 may be configured so as to be similar to any of the leg bands, side flaps, barrier cuffs, or elastic cuffs described above, each elasticized leg cuff 32 comprises a gasketing cuff as described in the above-referenced U.S. Pat. No. 3,860,003.

The diaper 20 preferably further comprises an elastic waist feature 34 that helps provide improved fit and containment. The elastic waist feature 34 is that portion or zone of the diaper 20 which is intended to elastically expand and contract to dynamically fit the wearer's waist. The elastic waist feature 34 preferably extends longitudinally outwardly from at least one of the waist edges 70 of the absorbent core 28 and generally forms at least a portion of the end edge 58 of the containment assembly 22. Disposable diapers are generally constructed so as to have two elastic waist features, one positioned in the first waist region 50 and one positioned in the second waist region 52, although diapers can be constructed with a single elastic waist feature. Further, while the elastic waist feature 34 or any of its constituent elements can comprise a separate element affixed to the diaper 20, the elastic waist feature 34 may be constructed as an extension of other elements of the diaper such as the backsheet 26 or the topsheet 24, preferably both the backsheet 26 and the topsheet 24. The waist feature 34 may be constructed in a number of different configurations including those described in U.S. Pat. No. 4,515,595 issued to Kievit et al. on May 7, 1985 and the above referenced U.S. Pat. No. 5,151,092 issued to Buell; each of these references being incorporated herein by reference.

In a preferred embodiment of the present invention, the diaper 20 also comprises ear flaps 62 that extend laterally outwardly from each longitudinal edge 56 of the containment assembly 22 in the second waist region 52. The ear flaps 62 provide a structure to which the first waist region 50 can be attached to encircle the legs and waist of the wearer. The ear flaps 62 may take on a number of different sizes, shapes, configurations, and materials. The ear flaps 62 may comprise a portion of the material making up one or more of the diaper elements, including the topsheet 24, and the backsheet 26. Alternatively, the ear flaps 62 may comprise a separate element or a plurality of elements affixed to the diaper. Suitable materials for use as the ear flaps 62 include woven webs; nonwoven webs; films, including polymeric films; foams; laminate materials including film laminates, nonwoven laminates, or zero strain laminates; elastomers; composites; or any combination of materials herein described or as described with respect to the extensible side panels as are known in the art. The ear flaps 62 may be joined to the containment assembly 22 by any means as known in the art; for example the ear flaps 62 may be continuously or intermittently bonded to the containment assembly using heated or unheated adhesive, heat bonding, pressure bonding, ultrasonic bonding, dynamic mechanical bonding or any other method that is known in the art.

The diaper 20 additionally comprises an extensible side panel 30 disposed adjacent each longitudinal edge 56 of the containment assembly 22 of the diaper 20, preferably in the first waist region 50. (As used herein, the term "disposed" means that an element(s) of the absorbent article is formed (joined and positioned) in a particular place or position as a unitary structure with other elements of the absorbent article or as a separate element joined to another element of the absorbent article.) The extensible side panels 30 provide an elastically extensible feature that provides a more comfortable and contouring fit by initially conformably fitting the diaper to the wearer and sustaining the fit throughout the time of wear well past when the diaper has been loaded with exudates since the extensible side panels 30 allow the sides of the diaper 20 to expand and contract. The extensible side panels 30 further provide more effective application of the diaper since even if the diaperer fits the diaper to the wearer asymmetrically, the diaper will "self-adjust" during wear to attain an improved fit. The extensible side panels 30 of the present invention also provide improved dynamic fit about the waist as well as the thigh of the wearer, reducing the possibility of sagging and gapping both at the waist and about the leg that can cause leakage, while increasing freedom of motion and wearer comfort in each area.

Each extensible side panel 30 comprises a waist panel 36 and a thigh panel 38. The waist panel 36 preferably has a different primary direction of extensibility than the thigh panel 38, providing the extensible side panel 30 with unique multi-directional stretch characteristics. The waist panel 36 is that portion or element of the extensible side panel 30 designed to initially provide the tension to secure the diaper 20 about the waist of the wearer, and once "activated", to dynamically expand and contract with the motions of the wearer to maintain the waist of the diaper in a snug, yet comfortable fit throughout the period of use. (As used herein, the term "activate" or "activated" means to apply tension to an extensible material in a relaxed condition such that the extensible material is no longer in a relaxed condition and thus, may expand and contract with the motions of the wearer.) The waist panel 36 is disposed longitudinally outboard of the thigh panel 38 and forms a portion of the waist encirclable edge 51. The waist panel 36 has a waist panel proximal edge 72, a waist panel distal edge 74 laterally opposed to the waist panel proximal edge 72, a first lateral edge 90 extending between the waist panel proximal edge 72 and the waist panel distal edge 74, and a second lateral edge 92 longitudinally opposed to the first lateral edge 90. In one preferred embodiment, the waist panel 36 is positioned so that the first lateral edge 90 is positioned farther from the transverse centerline 102 of the containment assembly 22 than the second lateral edge 92 and forms a part of the end edge 58 of the containment assembly 22.

Figure 4:
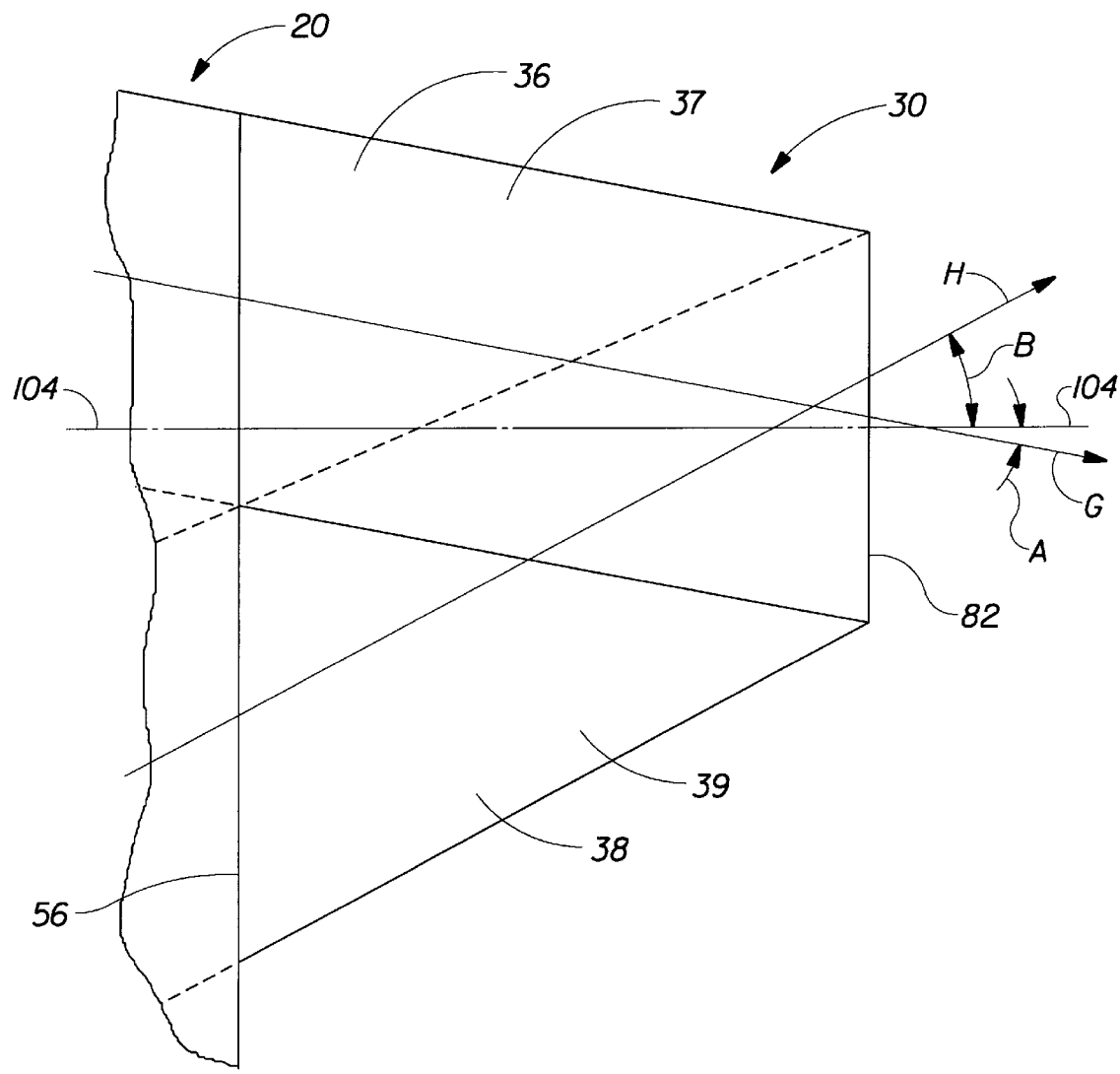
FIG. 4 is an enlarged, fragmentary plan view of the inner surface of the extensible side panel of the diaper shown in FIG. 1 showing the waist panel's primary direction of extensibility and the thigh panel's primary direction of extensibility with respect to a lateral axis. The tape tab and the stiffening members shown in FIG. 1 have been deleted for clarity.

The waist panel 36 comprises an extensible material preferably having a primary direction of extensibility (represented by arrow G) about the waist of the wearer. In one preferred embodiment, the waist panel's 36 primary direction of extensibility comprises a first vector component oriented laterally outwardly that is greater than zero and a second vector component that is greater than or equal to zero and is oriented towards the lateral centerline 102. More preferably, the first vector component of the waist panel's primary direction of extensibility is greater than the second vector component. (It should be noted, however, that the whole or segments of the waist panel 36 may also be extensible in directions other than the primary direction of extensibility.) Angle A in FIG. 4 represents the angle (measured clockwise or counterclockwise) between the waist panel's 36 primary direction of extensibility and the lateral axis 104 which is parallel to the lateral centerline 102. (In FIG. 4, angle A is measured in a clockwise direction from the lateral axis 104.) Angle A is preferably between about 0 and 45 degrees from the lateral direction, more preferably between about 5 and 20 degrees from the lateral direction, and most preferably between about 10 and about 15 degrees from the lateral direction.

The thigh panel 38 is that portion or element of the extensible side panel 30 designed to expand and contract with the dynamic motions of the wearer in the outer thigh region where the diaper encircles the wearer's leg. The thigh panel 38 forms a portion of the leg encirclable edge 53. The thigh panel 38 has a thigh panel proximal edge 78, a thigh panel distal edge 76 laterally opposed to the thigh panel proximal edge 78, a first lateral edge 94 extending between the thigh panel proximal edge 78 and the thigh panel distal edge 76, and a second lateral edge 96 longitudinally opposed to the first lateral edge 94. Preferably, the thigh panel 38 is disposed adjacent the longitudinal edge 56 of the containment assembly 22 and extends laterally outwardly from a location closer to the transverse centerline 102 of the containment assembly 22 than the waist panel 36. Preferably, the second lateral edge 96 of the thigh panel 38 is positioned farther from the end edge 58 of the containment assembly 22 than the first lateral edge 94. In a preferred embodiment, when the diaper 20 is fitted to the wearer, the second lateral edge 96 forms a part of the diaper 20 that encircles the thigh of the wearer.

The thigh panel 38 preferably comprises an extensible material having a primary direction of extensibility (represented by arrow H) nonparallel to the waist panel's primary direction of extensibility, preferably at an angle to the lateral and the longitudinal directions. In one preferred embodiment, the thigh panel's primary direction of extensibility comprises a first vector component oriented laterally outwardly that is greater than zero and a second vector component that is greater than or equal to zero and is oriented away from the lateral centerline 102. (The whole or segments of the thigh panel may also be extensible in directions other than the primary direction of extensibility.) As shown in FIG. 4, angle B represents the angle between the thigh panel's primary direction of extensibility and the lateral axis 104. (As used herein, the angle B is measured counterclockwise from the lateral axis 104.) Angle B is preferably between about 0 and 40 degrees from the lateral direction, more preferably between about 10 and 35 degrees from the lateral direction, and most preferably between about 20 and about 30 degrees from the lateral direction. In a preferred embodiment, when the diaper 20 is initially fitted to the wearer, the thigh panel 38 encircles the outer thigh portion of the wearer's leg. Once "activated", the thigh panel 38 dynamically expands and contracts in conjunction with the motions of the wearer's legs to maintain a snug fit about the leg of the wearer throughout the period of use. This improves the containment characteristics of the diaper while reducing the likelihood of red marks on the wearer's skin.

The waist panel 36 and the thigh panel 38, and thus, the extensible side panel 30, may take on a number of different sizes, shapes, configurations and materials. The exact length, width and thickness of the extensible side panel 30, as well as the waist panel 36 and the thigh panel 38, will vary depending on the dimensions of the intended user and the exact configuration of the extensible side panels 30. Accordingly, the waist panel 36 can be identical in size and shape to the thigh panel 38 or can have different dimensions so long as the waist panel 36 can be operatively associated to the thigh panel 38 and the containment assembly 22 of the diaper 20 to provide the multi-directional stretch characteristics of the invention as described herein. An example of suitable extensible side panels 30 to be worn by a medium sized infant are generally trapezoidal in shape having dimensions between about 2 and 4 inches in the longitudinal direction and between about 2 and 5 inches in the lateral direction.

The extensible side panels 30 may comprise a single piece of extensible material, or two or more extensible members operatively associated together to form each extensible side panel 30. As used herein, the terms "single component extensible side panel" or "single component embodiment" refers to embodiments of the present invention wherein the extensible side panel comprises a single extensible member. The terms "multiple-component extensible side panel" or "multiple component embodiment" are used herein to denote embodiments of the present invention wherein the extensible side panel 30 comprises two or more extensible members operatively associated together to form the extensible side panel 30. In a preferred embodiment, the extensible side panels 30 comprise more than one, preferably two, extensible members, a waist panel member 37 forming the waist panel 36 and a separate thigh panel member 39 forming the thigh panel 38. The extensible members can be constructed as extensions of other elements of the diaper such as the backsheet 26 or the topsheet 24, or both, or they can comprise wholly separate elements affixed to the containment assembly 22.

The proximal edge 80 of the extensible side panel 30 is disposed adjacent one longitudinal edge 56 of the containment assembly 22 of the diaper. In one configuration, the proximal edge 80 of the extensible side panel 30 is disposed between the topsheet 24 and the backsheet 26. However, the extensible side panel 30 can be joined to the containment assembly 22 in many different configurations. For example, the proximal edge 80 of the extensible side panel 30 can be joined to the outer surface 46 of the backsheet 26 or to the inner surface 44 of the topsheet 24. Alternatively, in a multiple component embodiment where the waist panel 36 and the thigh panel 38 comprise separate extensible members, the waist panel member 37 and the thigh panel member 39 can be disposed on the same or different surfaces, or between the topsheet 24 and the backsheet 26.

In yet other embodiments, the extensible side panel 30 or any of its components, can be disposed on a separate element that is joined to the containment assembly 22.

The extensible side panel 30 is preferably joined to the containment assembly 22 or to the diaper 20 by attachment means (not shown) such as those well known in the art. A suitable means for attaching each extensible side panel 30 to the containment assembly 22 is fusion bonding (e.g. ultrasonic, heat or pressure bonding). Alternatively, the extensible side panel 30 may be intermittently or continuously bonded to the containment assembly 22 using adhesive, dynamic mechanical bonding, or any other method that is known in the art.

In a preferred embodiment of the present invention as shown in FIGS. 1, 2, and 3, at least a portion of the waist panel 36 and the thigh panel 38 are joined together. Preferably, at least a portion of the waist panel distal edge 74 is joined to at least a portion of the thigh panel distal edge 76. In multiple component embodiments, it is preferred that the waist panel distal edge 74 and the thigh panel distal edge 76 are joined in at least a partially overlapping configuration. This ensures that forces applied to the first fastening member 40 disposed adjacent the distal edge 82 of the extensible side panel 30 will "activate" both the waist panel 36 and the thigh panel 38 such that they may expand and contract in conjunction with the motions of the wearer. The waist panel 36 and the thigh panel 38 may be bonded to each other using adhesive, heat bonding, pressure bonding, ultrasonic bonding, dynamic bonding, or any other method of bonding known in the art.

Figure 5:
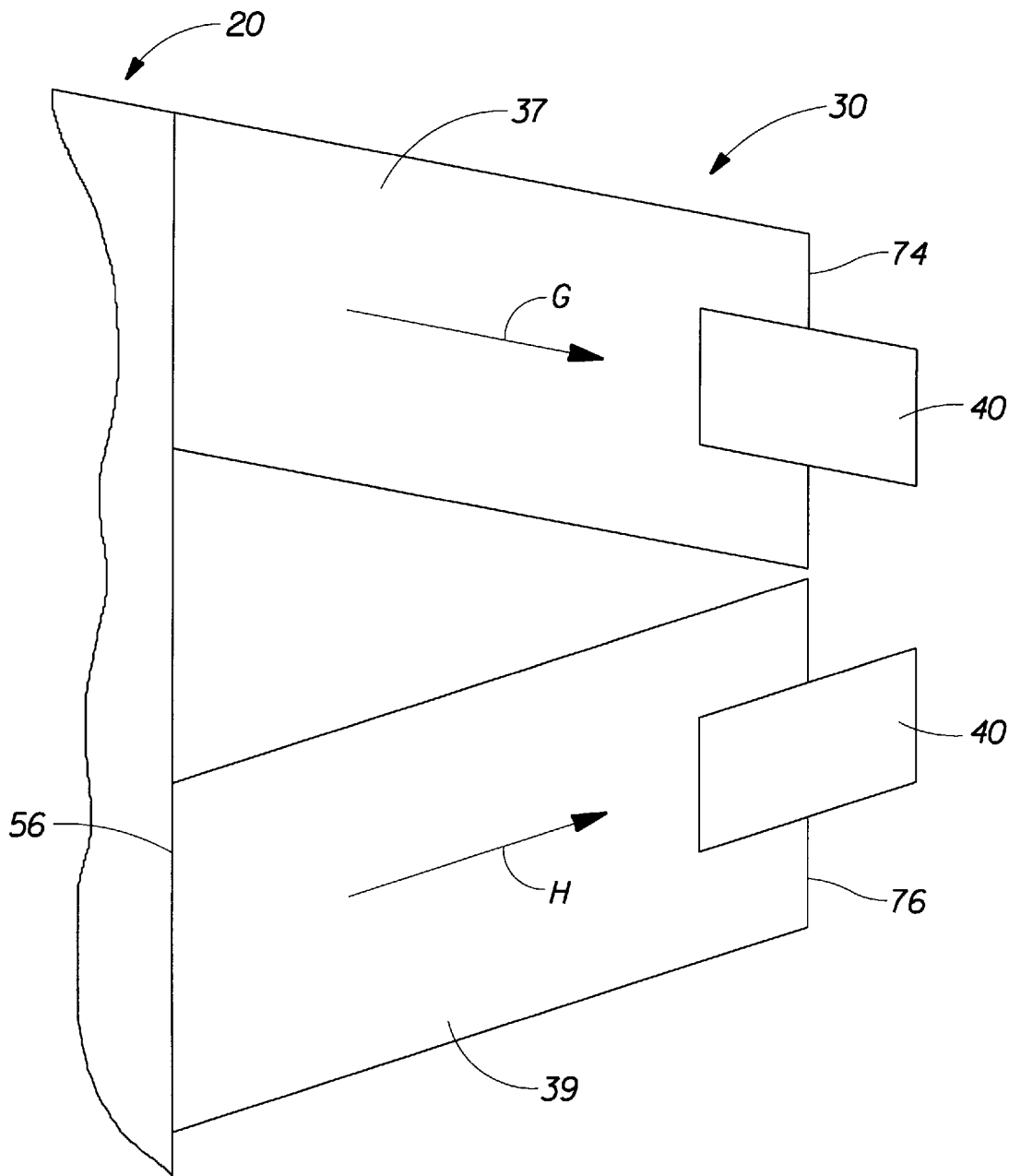
FIG. 5 is a plan view of a multiple component extensible side panel configuration wherein the distal edges of the waist panel and the thigh panel are not joined.

Alternatively, as shown in FIG. 5, a multiple component extensible side panel 30 is possible wherein the waist panel member 37 and the thigh panel member 39 are not initially joined to each other. The waist panel distal edge 74 is separate from the thigh panel distal edge 76, and each extensible member has a separate fastening component joined thereto. This gives the diaperer greater flexibility in the placement of the distal edges of the extensible members that form the waist panel member 37 and thigh panel member 39 when fastening the diaper 20 about the wearer. For example, in this configuration, the waist panel member 37 and the thigh panel member 39 can be individually fastened to the diaper 20 itself. Alternatively, the waist panel member 37 can be refastenably fastened to the thigh panel member 39 or the thigh panel member 9 can be refastenably fastened to the waist panel member 7. The waist panel member 37 and the thigh panel member 39 can be refastenably fastened to each other in a number of locations using the fastening components previously discussed with respect to the waist and thigh panel members or any other fastening members joined to the waist and thigh panel members, such as hook and loop type fasteners.

Each extensible side panel 30 may comprise any suitable extensible, stretchable or elastomeric materials. (As used herein, the term "extensible" refers to materials that can increase in at least one dimension. The term "stretchable" refers to materials that are extensible when stretching forces are applied to the material, and offer some resistance to extension. The term "elastomeric" refers to materials that extend in at least one direction when a force is applied and return to approximately their original dimensions after the force is released.) One elastomeric material that has been found to be especially suitable for use in the waist panel 36 and the thigh panel 38 is a laminate of two coverstock layers with an elastomeric film sandwiched between the coverstock layers. As used herein "coverstock" may include any woven or nonwoven materials. An example of a suitable coverstock material is the nonwoven material manufactured by Veratec, Inc., a Division of the International Paper Company, of Walpole, Mass., designated P-8. An example of a suitable film to be sandwiched between coverstock layers is the elastomeric film, EXX-500, (formerly EXX-7) manufactured by the Exxon Chemical Company of Lake Zurich, Ill. Other suitable materials for use as, or in the extensible side panels and side panel members include structural elastic-like film (SELF) webs, as described hereinbelow, synthetic or natural rubber, synthetic or natural rubber foams, elastomeric scrims, woven or nonwoven elastomeric webs, elastomeric composites such as elastomeric nonwoven laminates, zero strain stretch laminates, prestrained stretch laminates or the like. U.S. Pat. No. 5,151,092 entitled "Absorbent Article with Dynamic Elastic Waist Feature Having a Predisposed Resilient Flexural Hinge" issued to Buell et al., on Sep. 29, 1992 describes suitable zero stain stretch laminates and prestrained stretch laminates, and is herein incorporated by reference.

A structural elastic-like film (SELF) web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-path length which is greater than that of the other region as measured substantially parallel to the predetermined axis while the material is in an untensioned condition. The region exhibiting the longer surface-path length includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-path length to enter the plane of applied elongation, whereupon the SELF web exhibits second resistive forces to further elongation. The total resistive forces to elongation are higher than the first resistive forces to elongation provided by the first region.

The strainable web material can, in a preferred embodiment, comprise a formed polymeric film. The strainable web material can be made of a base material that has a relatively low extensibility under the forces the diaper is normally subjected to when worn. When formed into the strainable web material as described herein, however, the base material, thus formed, will be extensible under these forces. The strainable web material can also be formed into a structure that provides a "force wall" to be created at specific, pre-selected elongations and forces. The strainable web material is preferably comprised substantially of linear low density polyethylene (LLDPE). The strainable web material may also be comprised of other polyolefins such as polyethylenes, including low density polyethylene (LDPE), ultra low density polyethylene (ULDPE), high density polyethylene (HDPE), or polypropylene and blends thereof with the above and other materials. Examples of other suitable polymeric materials which may also be used include, but are not limited to polyester, polyurethanes, compostable or biodegradable polymers, heat shrink polymers, thermoplastic elastomers, and breathable polymeric structures.

The strainable web material can be used in various different forms in the extensible side panels 30 of the diaper 20. One example of a suitable form of structural elastic-like film is a laminate. The laminate comprises a strainable web material secured between two longitudinally extensible, preferably carded nonwoven webs. (In addition, the strainable web material can also be used in the various other components of the absorbent article described herein.)

Figure 6:
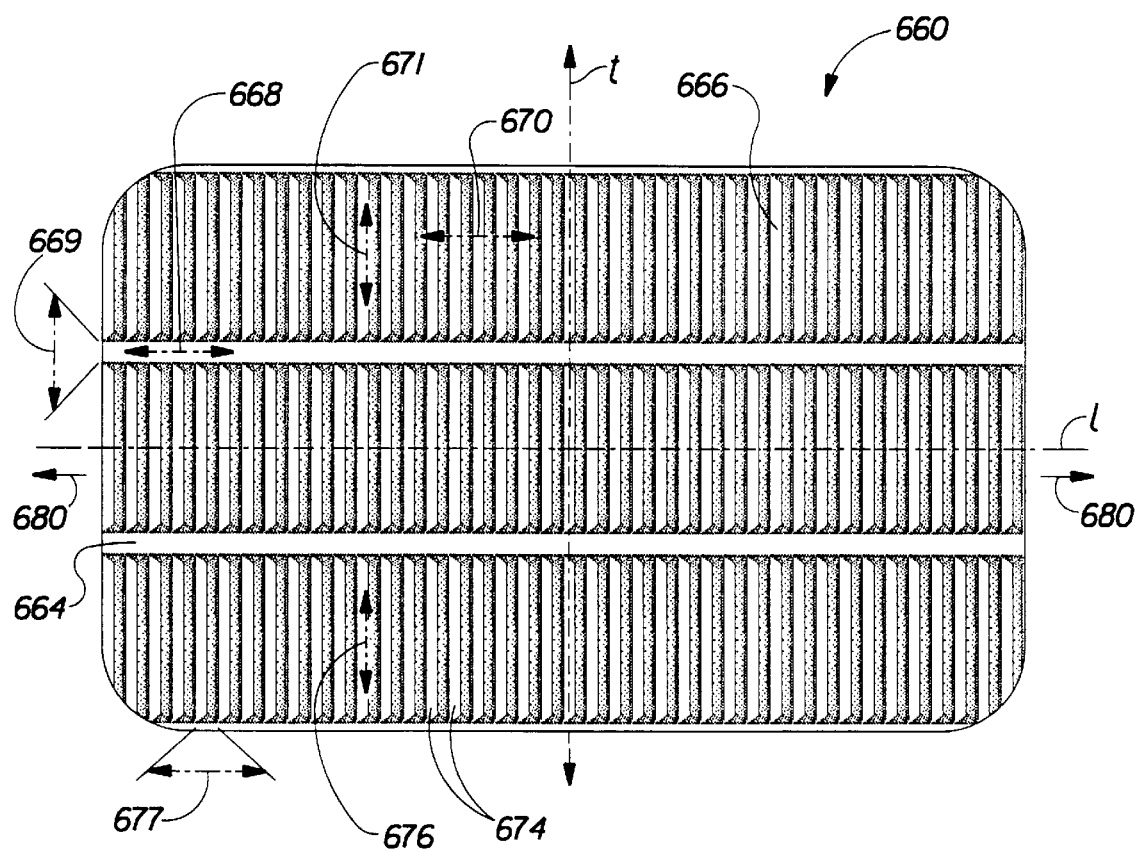
FIG. 6 is a plan view drawing of a preferred embodiment of a polymeric web material having a strainable network with the deformations facing toward the viewer.
Figure 7:
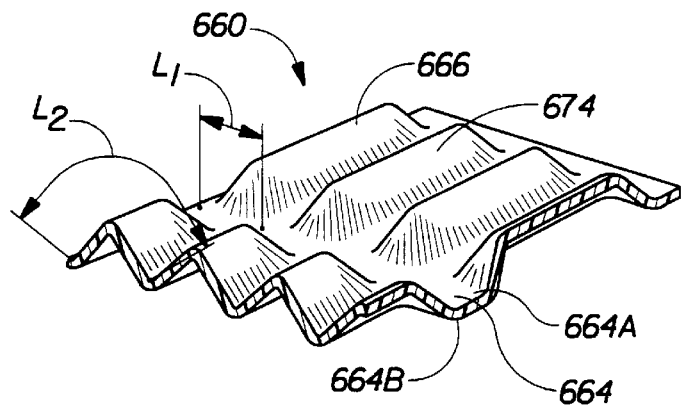
FIG. 7 is a segmented, perspective illustration of the polymeric web material of FIG. 6 in an untensioned condition.
Figure 8:
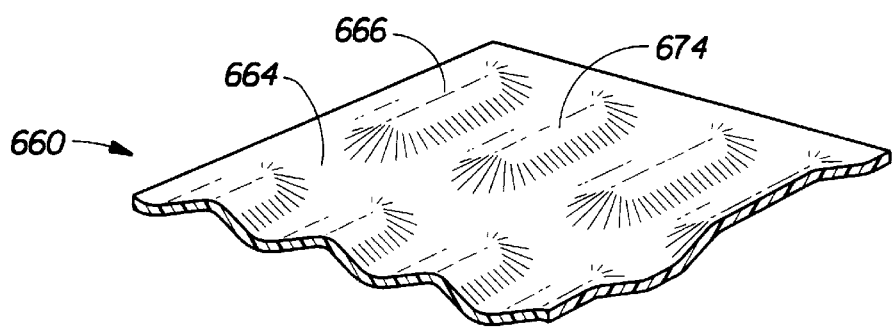
FIG. 8 is a segmented, perspective illustration of a polymeric web of FIG. 6 in a tensioned condition corresponding to stage I on the force-elongation curve depicted in FIG. 10.

The strainable web material is shown in FIGS. 6 and 7 in its substantially untensioned condition. The strainable web material has two centerlines, a longitudinal centerline, which is also referred to hereinafter as an axis or direction "l" and a transverse or lateral centerline, which is also referred to hereinafter as an axis or direction "t". The lateral centerline "t" is generally perpendicular to the longitudinal centerline "l". In a preferred embodiment, the longitudinal centerline 1 of the strainable web material is aligned with the longitudinal centerline 100 of the diaper 20. In other embodiments, however, the longitudinal centerline 1 of the web material can be oriented in other directions, depending on the direction of extensibility desired.

As shown in FIGS. 6 and 7, strainable web material 660 includes a "strainable network" of distinct and dissimilar regions. As used herein, the term "strainable network" refers to an interconnected and interrelated group of regions which are able to be extended to some useful degree in a predetermined direction providing the strainable web material with an elastic-like, relatively low resistive force stage and a relatively high resistive force stage. The strainable network includes at least a first region 664 and a second region 666. The first region 664 has an elastic modulus E1 and a cross-sectional area A1. The second region 666 has a modulus E2 and a cross-sectional area A2. The first and second regions each have a first surface and an opposing second surface. In the preferred embodiment shown in FIGS. 6 and 7, the strainable network includes a plurality of first regions 664 and a plurality of second regions 666. The first regions 664 have a first axis 668 and a second axis 669, wherein the first axis 668 is preferably longer than the second axis 669. The first axis 668 of the first region 664 is substantially parallel to the longitudinal axis, 1, of the strainable web material 660 while the second axis 669 is substantially parallel to the transverse axis, t, of the strainable web material 660. The second regions 666 have a first axis 670 and a second axis 671. The first axis 670 is substantially parallel to the longitudinal axis of the strainable web material, while the second axis 671 is substantially parallel to the transverse axis of the strainable web material. In the preferred embodiment of FIG. 6, the first regions 664 and the second regions 666 are substantially linear, extending continuously in a direction substantially parallel to the longitudinal axis of the strainable web material.

In the illustrated embodiment, a portion of the strainable web material has been "formed" such that the entire strainable web material exhibits a controlled resistive force along a predetermined axis (which in the case of the illustrated embodiment is substantially parallel to the longitudinal axis of the web material) when subjected to an applied axial elongation in a direction substantially parallel to the longitudinal axis. As used herein, the term "formed" refers to the creation of a desired structure or geometry upon the web material that will substantially retain the desired structure or geometry when it is not subjected to any externally applied elongations or forces. Suitable methods for forming a material such as the strainable web material described herein include, but are not limited to embossing by mating plates or rolls, thermoforming, high pressure hydraulic forming, or casting.

The web material used in the present invention is comprised of a strainable network of contiguous, "distinct", and "dissimilar" regions, wherein the strainable network includes at least a first region and a second region, where the first region has a "surface-path length" less than that of the second region. The surface path length is measured parallel to a predetermined axis when the material is in an untensioned state. As used herein, the term "formed portion" refers to the portion of the material which is comprised of the desired structure or geometry of the strainable network. As used herein, the term "surface-path length" refers to a measurement along the topographic surface of the region in question in a direction parallel to the predetermined axis. As used herein, the term "distinct" or "dissimilar" when referring to regions, refers to regions within the strainable network having measurably different surface-path lengths as measured parallel to a predetermined axis while the web material is in an untensioned condition.

In a preferred embodiment shown in FIGS. 6 and 7, the first regions 664 comprise a substantially planar region. That is, the material within the first region 664 is in substantially the same condition before and after the formation step undergone by strainable web material. The second regions 666 include a plurality of continuous, interconnected, deformations 674 which extend alternately beyond the plane of both the first and second surfaces (664A and 664B, respectively) of first region 664. In other embodiments, the deformations 674 may extend beyond the plane of only one of either the first or the second surfaces of the first region.

The deformations 674 have a first axis 676 which is substantially parallel to the transverse axis of the web material and a second axis 677 which is substantially parallel to the longitudinal axis of the strainable web material. The first axis 676 of the deformations 74 is at least equal to, and preferably longer than the second axis 677. To enhance the two-stage resistive force versus elongation behavior characteristics of (the side flap) of the present invention, the ratio of the first axis 676 to the second axis 677 is at least 1:1, and preferably at least 2:1 or greater. In general, the greater this ratio, the more pronounced will be the two-stage resistive force versus elongation characteristic of the web material.

The first region 664 and the second region 666 each have a "projected path length". As used herein the term "projected path length" refers to length of a region as viewed perpendicularly to the surface of the web material measured parallel to the predetermined axis (i.e., parallel to the longitudinal axis) of the strainable web material 660. The projected path length of the first region 664 and the projected path length of the second region 666 are equal to one another.

However, the first region 664 has a surface-path length, L1, less than the surface-path length, L2, of the second region 666 as measured topographically parallel to the longitudinal axis of the web material while the web material is in an untensioned condition. To enhance the two-stage resistive force versus elongation behavior characteristic of the strainable web material 660, the surface-path length of the second region 666 is at least about 15 percent greater than that of the first region, more preferably about 30 percent greater than that of the first region, and most preferably at least about 70 percent greater than that of the first region.

The web material 660 exhibits a modified "Poisson lateral contraction effect" substantially less than that of an otherwise identical unformed web material of the prior art. As used herein, the term "Poisson lateral contraction effect"

describes the lateral contraction behavior of a material which is being subjected to an applied elongation. Preferably the Poisson lateral contraction effect of the web material of the present invention is less than about 0.4 when the web is subjected to about 20 percent elongation. Preferably, the web material exhibits a Poisson lateral contraction effect less than about 0.4 when the web material is subjected to about 40, 50, or even 60 percent elongation. More preferably, the Poisson lateral contraction effect is less than about 0.3 when the web material is subjected to 20, 40, 50, or 60 percent elongation.

For the strainable web material, the direction of applied axial elongation, indicated by arrows 680, is substantially perpendicular to the first axis 676 of the deformations 674. (The amount of axial elongation is distance, D.) As the deformations 674 are able to extend in a direction substantially perpendicular to their first axis 676, the direction of applied axial elongation to cause extension in strainable web material is also substantially perpendicular to the first axis 676 of the deformations 674.

While the direction of applied axial elongation, indicated by arrows 680, is substantially perpendicular to the first axis 676 of the deformations 674, an applied axial elongation having a longitudinal component will cause the strainable web material to extend in the direction of applied axial elongation.

Figure 10:
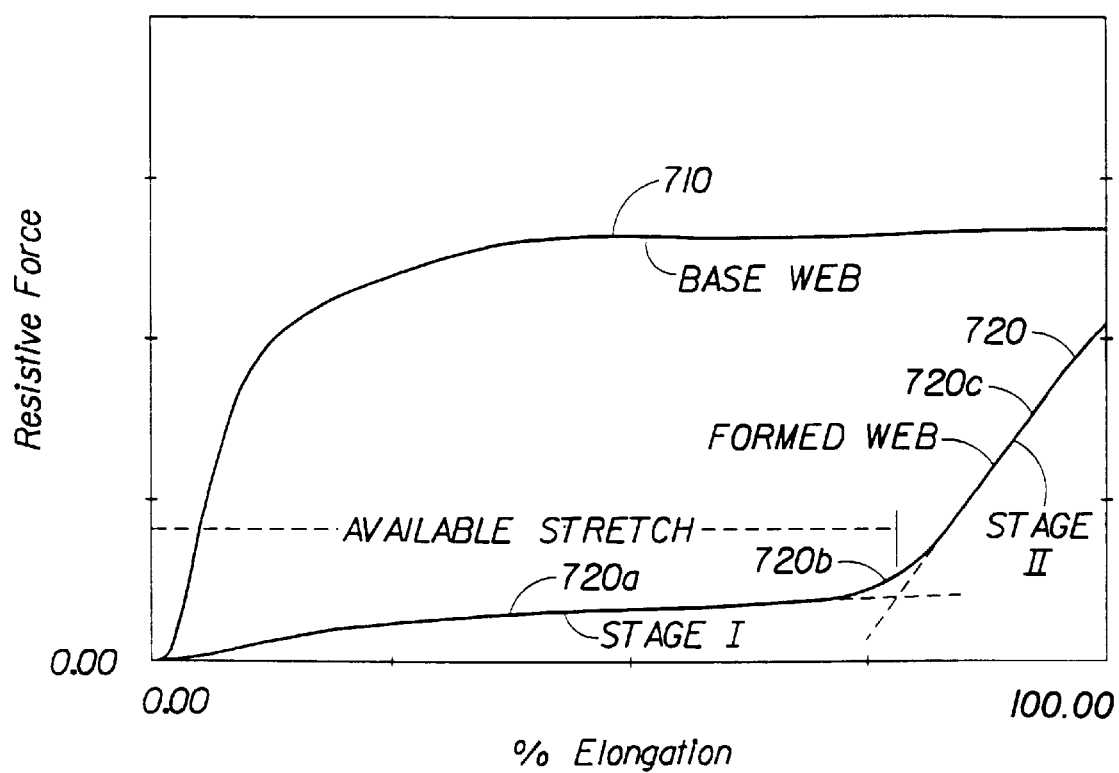
FIG. 10 is a graph of the resistive force verses percent elongation comparing the behavior of the polymeric web material of the present invention as shown in FIG. 6, with an otherwise identical, planar, base polymeric web material.

In FIG. 10 there is shown an exemplary graph of a resistive force-elongation curve 720 of a formed polymeric web material of the present invention along with a similar curve 710 for a planar, base polymeric film from which the web material is formed. Referring now to the force-elongation curve 720, there is an initial substantially linear, lower force versus elongation stage I designated 720*a*, a transition zone designated 720*b*, and a substantially linear stage II designated 720*c* which displays substantially higher force versus elongation behavior, corresponding to a resistive force wall beyond which the web material may undergo additional permanent deformation.

Figure 9:
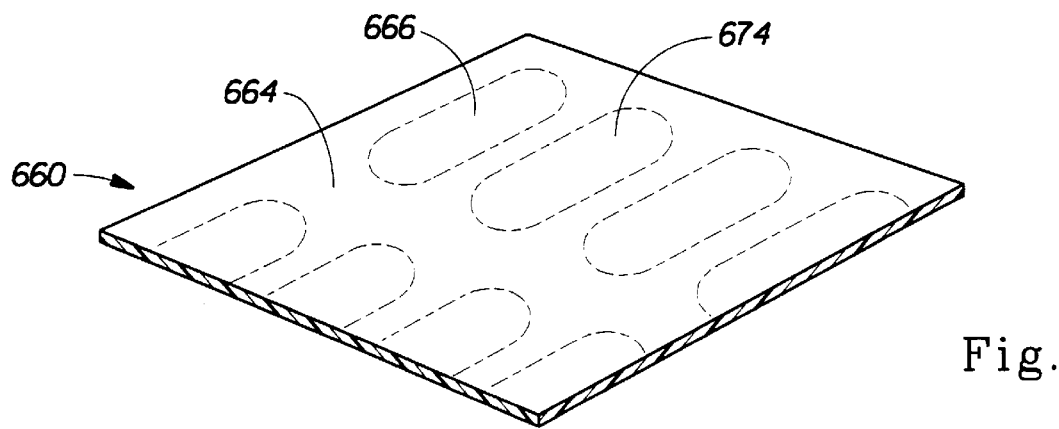
FIG. 9 is a segmented, perspective illustration of the polymeric web material of FIG. 6 in a tensioned condition corresponding to stage II on the force-elongation curve depicted in FIG. 10.

As seen in FIG. 10 a formed web material having a strainable network exhibits a controlled multi-stage behavior when subjected to an applied elongation in a direction parallel to the longitudinal axis of the web material. The resistive force to the applied elongation is significantly different between stage I (720*a*) and stage II (720*c*) of curve 720 as compared to curve 710 which does not exhibit this behavior. Referring now to FIG. 6, as the web material is subjected to an applied axial elongation indicated by arrows 680 in FIG. 6, the first region 664 having the shorter surface-path length, L1, provides most of the initial resistive force, P1, to the applied elongation which corresponds to stage I. While in stage I, the deformations 674 in the second region 666 are mostly out of the plane of applied elongation and offer minimal resistance to the applied elongation. In the transition zone between stages I and II, the deformations 74 are becoming aligned with the applied elongation. In stage II, as seen in FIG. 9, the deformations 674 in the second region 666 have become substantially aligned with the plane of applied elongation and begin to resist further elongation. The second region 666 now contributes a second resistive force, P2, to further elongation. The first and second resistive forces to elongation provide a total resistive force, PT, which is greater than the resistive force provided by the first region 664. Accordingly, the general slope of the force-elongation curve in stage II displays the characteristics of a force wall that is significantly greater than the general slope of the force-elongation curve in stage I.

The resistive force P1 is substantially greater than the resistive force P2 when (L1+D) is less than L2. While (L1+D) is less than L2 the first region 664 provides an initial resistive force, P1, generally satisfying the equation:

$$P1 = \frac{(A1 * E1 * D)}{L1}$$

When (L1+D) is greater than L2 the first and second regions provide a combined total resistive force, PT, to the applied elongation D, generally satisfying the equation:

$$PT = \frac{(A1 * E1 * D)}{L1} + \frac{(A2 * E2 * |L1 + D - L2|)}{L2}$$

(Where "*" represents a multiplication sign.)

The maximum elongation occurring while in stage I is considered to be the "available stretch" of the web material. The available stretch can be effectively determined by inspection of the force-elongation curve 720, the approximate point at which there is an inflection in the transition zone between stage I and stage II is the percent elongation point of "available stretch". The range of available stretch can be varied from about 10% to 100% or more; this range of elastic-like response is often found to be of interest in disposable absorbent articles, and can be largely controlled by the extent to which surface-path length L2 in the second region 666 exceeds surface-path length L1 in the first region 64 and the properties of the base film. Significantly higher forces are required to achieve percent elongations in the base film equivalent to those percent elongations in the web 660. The approximate extent of stage I can be controlled as desired by adjusting the path lengths, L1 and L2 in an untensioned condition. The force-elongation behavior of stage I can be controlled by adjusting the width, thickness, and spacing of first region 664 and the properties of the base film.

When the web material of FIG. 6 is subjected to an applied elongation, the web material exhibits an elastic-like behavior as it extends in the direction of applied elongation and retracts to its substantially untensioned condition once the applied force is removed, unless extended to the point of yielding. The web material is able to undergo multiple applications of applied elongation without losing its ability to substantially recover. Accordingly, the web material is able to retract to its substantially untensioned condition once the applied elongation or force is removed.

While the web material may be easily and reversibly extended in the direction of applied axial elongation, in a direction substantially perpendicular to the first axis 676 of the deformations 674, web material is relatively non-extensible in a direction substantially parallel to the first axis 676 of the deformations 674. The plastic deformation imparted upon the deformations 674 allows the deformations to be extended in one direction, in a direction substantially perpendicular to the first axis of the deformations, while being relatively non-extensible in a direction substantially perpendicular to the direction of extension, in a direction substantially parallel to the first axis of the deformations. In other embodiments, the strainable web material 660 can be provided with first regions 664 that extend outward from a center and second regions 666 that are disposed in concentric circles around the center to make the strainable web material 660 extensible in more than one direction.

The amount of applied force required to extend the web material is dependent upon the inherent properties of the base material forming the web material and the width and spacing of the undeformed regions 664, with narrower and more widely spaced undeformed regions 664 requiring lower extensional forces to achieve the desired elongation. The first axis 668, (i.e., the length) of the undeformed regions 664 is preferably greater than the second axis 669, (i.e., the width) with a preferred length to width ratio of between 5:1 and 300:1.

The depth and number of deformations 674 can also be varied to control the applied force or elongation required to extend the web material of the present invention. In one preferred embodiment, the deformations are formed by two rigid plates having outer dimensions of 5.0" by 12" by 0.75". On one surface of each plate are a series of meshing teeth which are substantially triangular in cross section and measure 0.030" at their bases and taper to a vertex with a radius of 0.008" at the top. The centerlines of the teeth are spaced evenly and at 0.030" increments. On the "toothed" side of one plate, a series of grooves are cut which are parallel to each other and perpendicular to the evenly spaced teeth. These grooves measure 0.031" wide and are continuous over the entire length of the plate, and are spaced at a distance of 0.25" on center. These grooves correspond to the undeformed regions of the deformed web of material.

The preferred LLDPE base material is placed between the plates in a hydraulic press having platens larger than the plates to evenly distribute pressure. The plates are compressed under a load of at least 4,000 pounds. The formed web material is then removed from between the plates. The available stretch or elongation is increased if for a given number of deformations, the height or degree of deformation imparted on the deformations is increased. Similarly, the available stretch or elongation is increased if for a given height or degree of deformation, the number or frequency of deformations is increased.

It has been found that the extension characteristics, including the extension forces, extension modulus, and available stretch (extension), and the contractive forces, elastic creep, elastic hysteresis, and rate of contraction of the extensible side panels 30 are important considerations in the performance of the extensible side panels 30 and the diaper 20. The extension characteristics give the diaperer and wearer the overall perceived "stretchiness" during use. They also affect the ability of the diaper to achieve a suitable degree of application stretch (i.e., for a "normally" perceived tension of the diaper during application,. the total amount of resultant stretch is that desired to achieve/maintain good conformity of fit). An extensible side panel with a relatively high extension modulus can cause red marking on the wearer's skin while relatively low extension modulus can cause sagging/slipping on the wearer. Side panels having too little available stretch may not achieve a suitable level of body conformity and may contribute in making the diaper uncomfortable to wear and hard to apply to the wearer. A diaper having extensible side panels with very low contractive forces may not stay in place on the wearer and they tend to sag/slip on the wearer resulting in poor fit and containment.

Typical extensible materials show a hysteresis loop of force in their stress-strain property. That is, for a given extension, the force (extension force) required to uniaxially extend the extensible material is greater than the force (contractive force) the extensible material exerts when it is allowed to contract from its preextended condition. The former curve can be referred to as the "load curve" and the latter curve can be referred to as the "unload curve". The "load" extension force (extension force) is felt by the diaperer when the extensible side panel is stretched to apply the diaper to the wearer. The wearer more nearly "feels" the "unload" forces (contractive forces) once the diaper is on. Therefore, the hysteresis loss should not be so great that the contractive force is low enough to allow sagging/gapping of the diaper on the wearer.

For the "composite extensible side panel" of the present invention, it has been found that the extension force, the contractive force, and the minimum amount of extension are preferably within defined ranges. (As used herein, the phrase "composite extensible side panel" refers to the extensible side panel as a whole, in any configuration and comprising any material or combination of materials.) The extension force to initially extend the composite extensible side panel is preferably between about 100 grams and about 1200 grams. More preferably, the extension force is between about 200 grams and about 1000 grams. When the composite extensible side panel is held in an extended state for about five minutes, it is preferred that the composite extensible side panel maintain a contractive force of between about 75 grams and about 900 grams, and more preferably between about 100 grams and about 850 grams. A composite extensible side panel having extension and contractive forces within these ranges will preferably provide at least about 0.15 inches of extension in the direction of the applied force.

The extensible side panels 30 may also be provided with differential extensibility along the longitudinal axis when stretched in the lateral direction. As used herein, the term "differential extensibility" is used to mean a material having a nonuniform degree of extensional properties, as measured in the direction of stretching at various points along an axis oriented substantially perpendicular to the direction of stretching. This may, for example, include varying the elastic modulus or available stretch, or both, for each of the extensible material(s). The differential extensibility can be achieved in a number of different ways. The extensible side panels 30 can have multiple combined extensible materials, multiple configurations for the extensible materials, or the extension properties of the extensible or other materials making up the extensible side panel may be nonuniform. For example, differential extensibility can be achieved in selected adjacent portions of the extensible side panel by using extensible materials having varying extensions or contractive forces, modulus, or other inherent properties such that more or less (varying) lateral extensibility is achieved in one portion of the extensible side panel 30 than the adjacent panel. The extensible materials may also have varying lengths, sizes, and shapes that provide differential extensibility. Other ways of varying the properties of materials that form the extensible side panels 30 as are known in the art may also be used.

The diaper 20 is also preferably provided with a fastening system 48 for fitting the diaper on the wearer. The fastening system 48 maintains the first waist region 50 and the second waist region 52 in an overlapping configuration to form a side closure. The fastening system 48 further maintains tension in both the waist panel 36 and thigh panel 38 to hold the diaper 20 on the wearer as well as to provide for improved dynamic fit about the legs and waist of the wearer. The fastening system 48 may comprise any attachment means known in the art, including, but not limited to, pressure sensitive adhesives, cohesive materials, mechanical fastening means, hook and loop type fasteners, or any combination of these or any other attachment means as known in the art. Examples of suitable adhesive tape tab fastening systems are disclosed in U.S. Pat. No. 3,848,594 issued to Buell on Nov. 19, 1974; and U.S. Pat. No. 4,662,875 issued to Hirotsu and Robertson on May 5, 1987;

each of which are incorporated herein by reference. Examples of other closure systems, including mechanical closure systems, useful in the present invention are disclosed in U.S. Pat. No. 4,869,724 issued to Scripps on Sep. 26, 1989; U.S. Pat. No. 4,846,815 issued to Scripps on Jul. 11, 1989; and U.S. Pat. No. 5,242,436 issued to Weil, Buell, Clear, and Falcone on Sep. 7, 1993; each of which are incorporated herein by reference.

As shown in FIG. 1, the fastening system 48 preferably comprises at least one pair of first fastening members 40 having a primary centerline F, and at least one second fastening member 42. The primary centerline F of the first fastening member is generally parallel to the line of tension normally applied to the extensible side panel 30 when fitting the diaper 20 to the wearer. The primary centerline F of the first fastening member 40 is preferably at an angle to both the longitudinal centerline L and the transverse centerline 102 of the diaper 20 in its uncontracted state. In a preferred embodiment, one first fastening member is disposed on the inner surface 44 of each extensible side panel 30 adjacent the distal edge 82. The first fastening members 40 are preferably joined to the distal edge 82 of each extensible side panel 30, preferably overlapping the boundary between the waist panel 36 and the thigh panel 38. This ensures that the first fastening member 36 provides tension to "activate" both the waist panel 36 and the thigh panel 38, thereby allowing the panels to more dynamically expand and contract with the motions of the wearer. The second fastening member 42 is preferably disposed on the outer surface 46 of the containment assembly 22 in the second waist region 52 and is engageable with the first fastening member 40.

In a particularly preferred embodiment, the diaper 20 comprises at least one proximal "stiffening member" 84 disposed adjacent the proximal edge 80 of each extensible side panel 30. As used herein, the term "stiffening member" means any element of the diaper, any element of the extensible side panel 30, or any other element joined to the extensible side panel 30 or to the containment assembly 22 of the diaper 20, or both, that provides compression/buckling resistance in at least one direction. The compression/buckling resistance provided by the proximal stiffening member 84 reduces bunching of the diaper 20, preferably in the longitudinal direction, along the longitudinal edges 56 of the containment assembly 22 in the first waist region 50. The proximal stiffening member 84 also reduces the tendency of the end edge 58 of the containment assembly 22 located in the first waist region 50 and the waist feature 34 from rolling over as a result of the dynamic motions of the wearer. Thus, the proximal stiffening member 84 reduces the likelihood of gapping in the waist regions of the diaper 20 and increases the effectiveness of the multi-directional extensible side panels 30 by providing an improved dynamic fit about the waist and thigh of the wearer.

While the proximal stiffening member 84 may be positioned between the topsheet 24 and the backsheet 26, the proximal stiffening member 84 may alternatively be positioned on the outer surface 46 of the backsheet 26, on the inner surface 44 of the topsheet 24, or in a number of other configurations. The proximal stiffening member 84 may take also on a number of different sizes, shapes, configurations, and materials. For example, the proximal stiffening member 84 may be formed from one or a plurality of stiffening components, and the proximal stiffening member 84 may have varying widths, lengths, thicknesses, and shapes. The proximal stiffening member 84 preferably comprises a portion of the material making up one or more of the diaper's elements, including the topsheet 24, the backsheet 26, or the material or materials used in the extensible side panels 30. Alternatively, the proximal stiffening member 84 may comprise a separate piece of material positioned adjacent the proximal edge 80 of the extensible side panel 30. Suitable materials for use as the proximal stiffening member 84 of the present invention include woven webs, nonwoven webs, films, formed films, foams, laminate materials including film laminates or nonwoven laminates of two or more nonwoven layers, screens, corrugated materials that provide stiffness in at least one direction, and any combination of the above materials or other materials as are known in the art. The proximal stiffening member 84 may be joined to the containment assembly 22 by any means known in the art.

In another preferred embodiment, the diaper additionally comprises a distal stiffening member 86 disposed adjacent the distal edge 82 of the extensible side panel 30. Preferably, the distal stiffening member 86 is joined to both the waist panel 36 and the thigh panel 38. In this configuration, the distal stiffening member 86 distributes any tension or forces applied to the distal edge 82 of the extensible side panel 30 throughout both the waist panel 36 and the thigh panel 38. The distal stiffening member 86 also provides compression/buckling resistance, preferably along the longitudinal direction in the distal edge 82 of the extensible side panel 30, that reduces the possibility that the distal edge 82 of the extensible side panel 30 will buckle or fold when the wearer moves. Thus, in a preferred embodiment, a distal stiffening member 86 disposed adjacent the distal edge 82 of the extensible side panel 30 will ensure that the diaper fits the wearer properly and that the waist panel 36 and the thigh panel 38 are properly positioned to expand and contract in conjunction with the dynamic movements of the wearer. As with the proximal stiffening member 84, the distal stiffening member 86 can take on a number of different sizes, shapes, configurations, and materials. The distal stiffening member 86 may be formed from one or a plurality of stiffening components, and the distal stiffening member 86 may have varying widths, lengths, thicknesses, and shapes. In a preferred embodiment, the distal stiffening member 86 comprises a portion of the material making up the extensible side panels 30 or another element of the diaper 20. Alternatively, the distal stiffening member 86 may comprise a separate piece of material positioned adjacent the distal edge 82 of the extensible side panel 30. The materials suitable for use in the distal stiffening member 86 and the methods for joining the distal stiffening member 86 to the diaper 20 are described hereinbefore with respect to the proximal stiffening member 84.

The diaper 20 is preferably applied to a wearer by positioning one of the waist regions, preferably the first waist region 52, under the wearer's back and drawing the remainder of the diaper 20 between the wearer's legs so that the other waist region, preferably the second waist region 50, is positioned across the front of the wearer. The diaperer then wraps one extensible side panel 30 around the wearer, while grasping one of the first fastening members 40 disposed on each of the extensible side panels 30. In the embodiment wherein at least a portion of the waist panel 36 and thigh panel 38 are joined together, the tension created by wrapping the extensible side panel 30 around the wearer activates both the waist panel 36 and thigh panel 38 (dual-activation), allowing them to expand and contract in conjunction with the movements of the wearer. (In embodiments where the waist and thigh panel members are not joined together, dual-activation takes place as the diaperer applies tension separately to the individual waist and thigh panel members.) The diaperer then repeats this step for the other extensible side panel 30. The waist closure is formed by engagement of the first fastening members 40 to the second fastening member 42 located in the second waist region 52. With the formation of the waist closure, the diaper 20 is initially conformably fit about the wearer. If the diaper 20 has been fitted asymmetrically, the diaper 20 will self-adjust during wear to attain an improved fit. Once fitted to the wearer, the multi-directional extensible side panels 30 expand and contract in conjunction with the motions of the wearer to provide improved dynamic fit throughout the time of wear, well past when the diaper 20 has been loaded with exudates. This improved dynamic fit reduces sagging and gapping of the diaper 20 in the waist and thigh regions while increasing wearer comfort.

Figure 11:
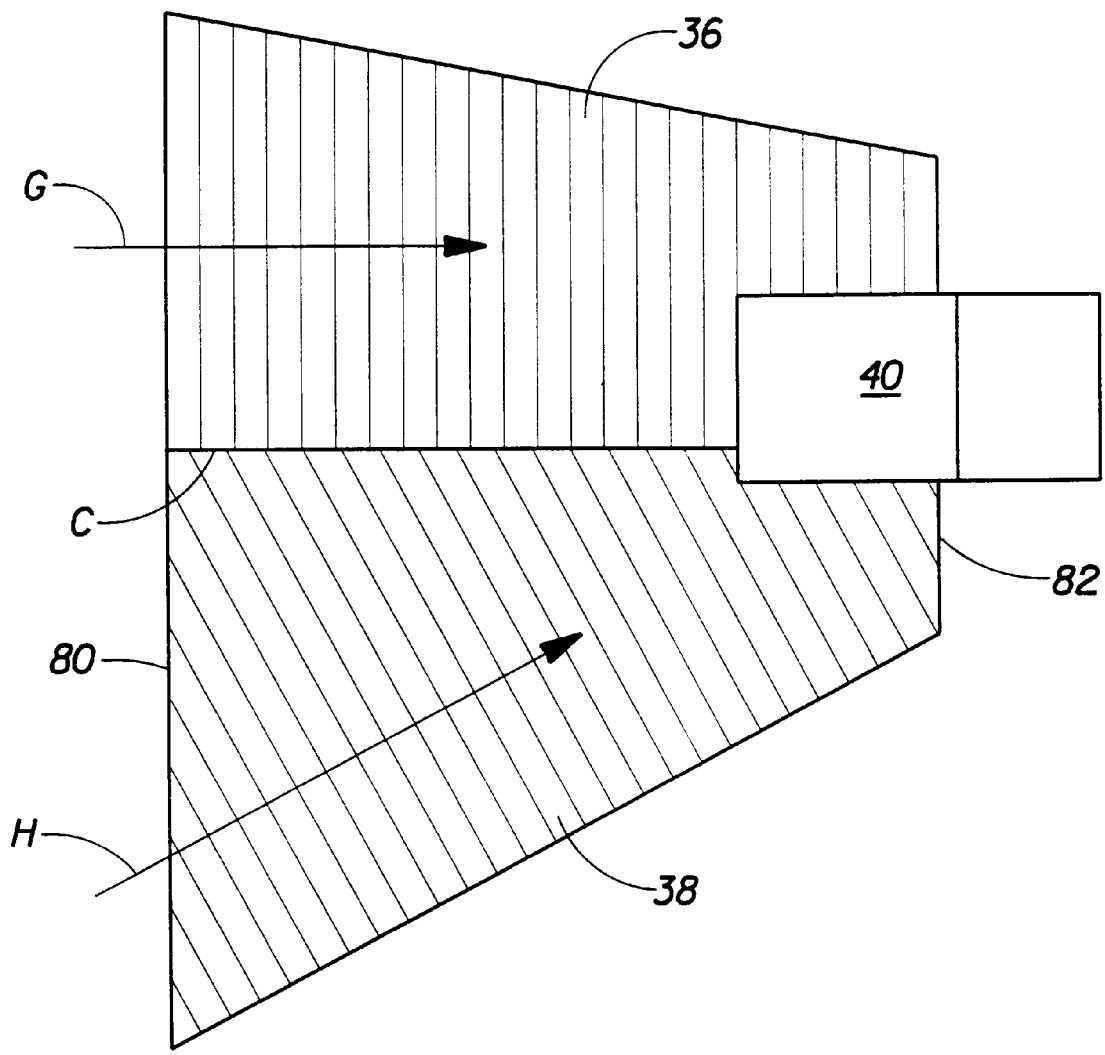
FIG. 11 is an enlarged, fragmentary plan view of an alternative embodiment of the present invention wherein the extensible side panel comprises a single component.

FIG. 11 shows one alternative embodiment of the present invention having a single component extensible side panel. The extensible side panel of this embodiment is designated 30. The extensible side panel 30 comprises a single piece of extensible material wherein a first portion of the extensible side panel 30 forms the waist panel 36 and a second portion forms the thigh panel 38. The extensible material can comprise a single layer material or a laminate of two or more layers of materials that have been joined together. The multi-directional stretch characteristics of the single piece extensible side panel 30 are preferably achieved by performing a mechanical operation, such as pleating, corrugation, or ring-rolling, on the material to produce areas of different extensible behavior. One preferred mechanical operation suitable for providing multi-directional stretch characteristics in a material to be used in the extensible side panel 30 is described above with respect to structural elastic-like film webs. Alternatively, the extensible side panel 30 can be constructed out of extensible materials having areas of different elastic behavior achieved by means other than the aforementioned mechanical operations, such as slitting, cutting, bonding or folding the extensible material that forms the extensible side panel. In such embodiments, the slits, folds, bonds or cuts in the material are not limited to any particular sizes or shapes. For example, the material making up the extensible side panel 30 may be fully or partially severed or may have portions cut out or bonded to create different extensibility characteristics in the extensible side panel 30. (As used herein, the term "fully severed" refers to single component extensible side panels 30 having a cut or slit running the entire distance between the proximal edge 80 to the distal edge 82 of the extensible side panel 30. The term "partially severed" refers to single component extensible side panels 30 that having a cut or slit that does not extend from the proximal edge 80 to the distal edge 82 of the extensible side panel 30.)

In a preferred embodiments, the waist panel 36 preferably has a primary direction of extensibility G about the wearer's waist. The thigh panel 38 preferably has a primary direction of extensibility H at an angle to the lateral and the longitudinal about the thigh of the wearer. FIG. 11 shows an embodiment of the single piece extensible side panel 30 comprising a distinct boundary line between the waist and thigh panels that defines where the elastic characteristics of each panel begins and ends. (The boundary line is denoted by the line C in FIG. 11.) The boundary between the waist panel 36 and the thigh panel 38 may be positioned anywhere on the extensible side panel. However, extensible side panels are contemplated wherein there is no distinct boundary between the waist and thigh panels. For example, the extensible side panel may be constructed such that areas of different elastic behavior partially overlap or do not meet at a common boundary.

Figure 12:
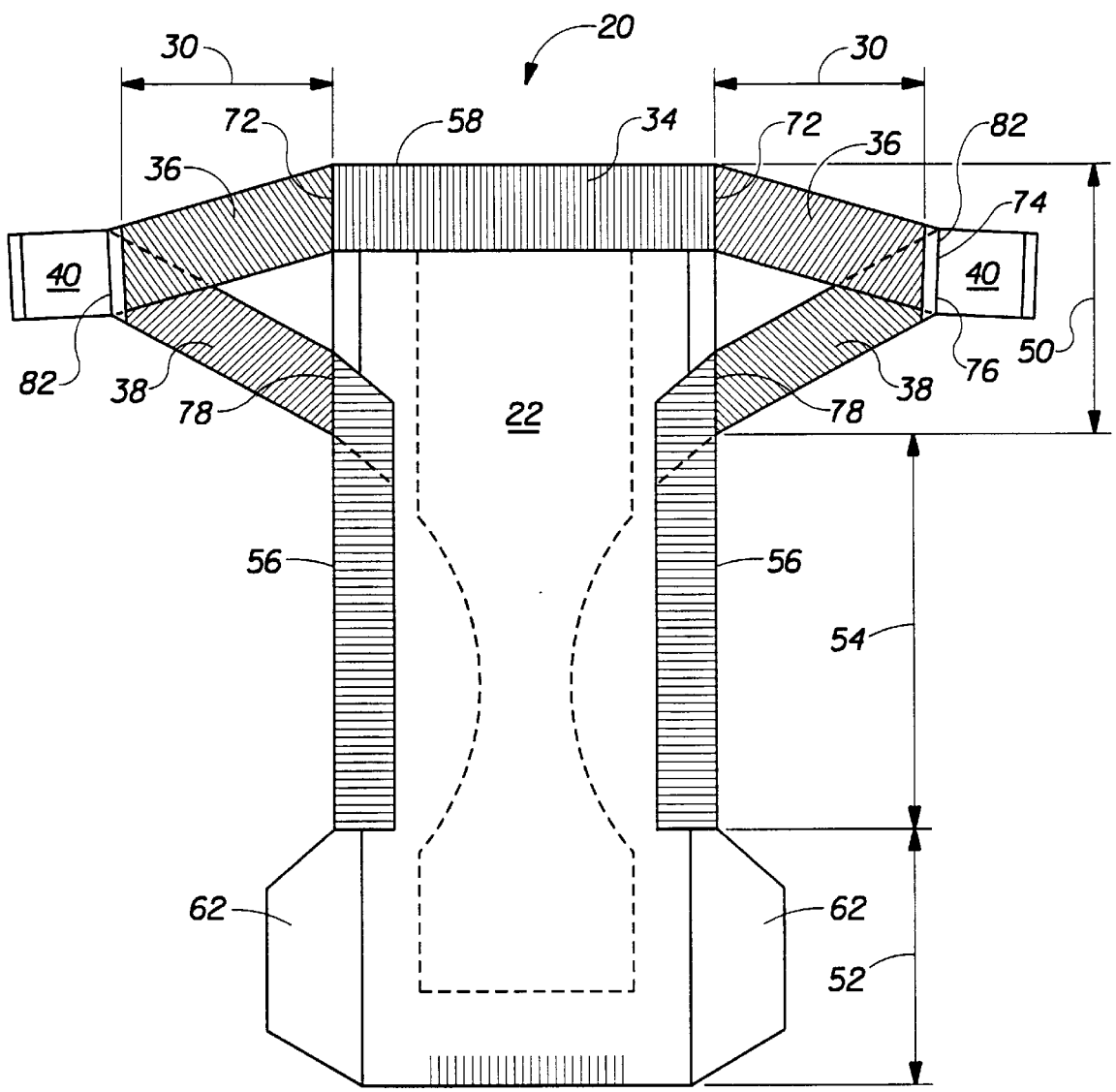
FIG. 12 is a plan view of an alternative embodiment of the present invention wherein a single extensible component is folded to form the extensible side panels as well as the waist feature and the leg cuffs of the disposable absorbent article.

FIG. 12 shows an alternative single component embodiment of the present invention having a single piece of extensible material joined to the containment assembly 22 of the diaper 20 and folded such that the extensible material extends throughout both of the multi-directional extensible side panels 30, the waist feature 34 and at least a portion of the crotch region 54 of the diaper 20. The extensible material may be uniform throughout or may have areas with different extensibility characteristics. In one embodiment, the extensible material extends along at least a portion of the crotch region 54 of the containment assembly 22 of the diaper 20 juxtaposed at least one longitudinal edge 56. In the first waist region 50, the extensible material is folded to form the thigh panel proximal edge 78. From the thigh panel proximal edge 78, the extensible material extends outwardly from the containment assembly 22, preferably at an angle to the lateral and the longitudinal directions. The outwardly extending extensible material forms the thigh panel 38 and is folded inwardly at a point spaced laterally outwardly from the longitudinal edge 56 of the containment assembly 22. The fold preferably forms the distal edge 82 of the extensible side panel 30 as well as the waist panel distal edge 74 and the thigh panel distal edge 76. The inwardly folded extensible material extends from the distal edge 82 of the extensible side panel 30 to a location on the longitudinal edge 56 of the containment assembly 22 in the second waist region 52 adjacent to the end edge 58, forming the waist panel 36. From the waist panel proximal edge 72 (where the waist panel 36 joined to the containment assembly 22), the extensible material extends laterally across the first waist region 50 adjacent to the end edge 58 of the diaper 22. The same piece of extensible material further extends laterally outwardly from the other longitudinal edge 56 of the containment assembly 22 and is folded as previously described to form the waist panel 36 and the thigh panel 38 of the opposing extensible side panel 30 as well as at least a portion of the crotch portion 54 of the containment assembly 22.

Other alternative embodiments are also contemplated wherein a single piece of extensible material extends through multiple components of the diaper 22. In one preferred alternative embodiment, a single piece of extensible material is folded to form only the waist panel 36 and thigh panel 38. In this configuration, the waist panel distal edge 74 and the thigh panel distal edge 76 are formed by the fold in the extensible material. The waist panel 36 and the thigh panel 38 extend from the fold (distal edge of extensible side panel 82) to the containment assembly 22. Incorporating a single piece of extensible material into multiple components of a diaper has the advantage of reducing the number of individual elastic components that must be separately formed and attached to the containment assembly.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article to be fitted to a wearer having a first waist region, a second waist region, a waist encirclable edge, a first leg encirclable edge, a second leg encirclable edge, a lateral centerline, a lateral direction parallel to the lateral centerline, a longitudinal centerline and a longitudinal direction parallel to the longitudinal centerline, the absorbent article further comprising:

a) a containment assembly having a first longitudinal edge and a second longitudinal edge, a portion of said first longitudinal edge forming a portion of said first leg encirclable edge and a portion of said second longitudinal edge forming a portion of said second leg encirclable edge, a first end edge disposed in said first waist region and a second end edge disposed in said second waist region, said first end edge forming a portion of said waist encirclable edge and said second end edge forming a portion of said waist encirclable edge, said first longitudinal edge and said second longitudinal edge extending from said first end edge to said second end edge, said containment assembly further comprising an absorbent core;

b) an elastomeric first side panel disposed along said first longitudinal edge of said containment assembly in said first waist region and projecting laterally outwardly therefrom, said elastomeric first side panel comprising a first waist panel and a first thigh panel, said first waist panel having a first waist panel proximal edge and a first waist panel distal edge spaced laterally outwardly from said first waist panel proximal edge so as to be disposed laterally outboard of said first longitudinal edge, said first waist panel proximal edge having a portion disposed adjacent said first end edge of said containment assembly, said first thigh panel having a first thigh panel proximal edge and a first thigh panel distal edge spaced laterally outwardly from said first thigh panel proximal edge so as to be disposed laterally outboard of said first longitudinal edge of said containment assembly, a portion of said first thigh panel being overlapped with and joined to a portion of said first waist panel, said first waist panel being longitudinally outboard of said first thigh panel and forming a portion of said waist encirclable edge, said first thigh panel forming a portion of said first leg encirclable edge, said first waist panel having a first direction of extensibility and said first thigh panel having a second direction of extensibility when a force is applied to said elastomeric first side panel, said second direction of extensibility being nonparallel to said first direction of extensibility; and c) an elastomeric second side panel disposed along said second longitudinal edge of said containment assembly in said first waist region and projecting laterally outwardly therefrom, said elastomeric second side panel comprising a second waist panel and a second thigh panel, said second waist panel having a second waist panel proximal edge and a second waist panel distal edge spaced laterally outwardly from said second waist panel proximal edge so as to be disposed laterally outboard of said second longitudinal edge of said containment assembly, said second waist panel proximal edge having a portion disposed adjacent said first end edge of said containment assembly, said second thigh panel having a second thigh panel proximal edge and a second thigh panel distal edge spaced laterally outwardly from said second thigh panel proximal edge so as to be disposed laterally outboard of said second longitudinal edge of said containment assembly, a portion of said second thigh panel being overlapped with and joined to a portion of said second waist panel, said second waist panel being longitudinally outboard of said second thigh panel and forming a portion of said waist encirclable edge, said second thigh panel forming a portion of said second leg encirclable edge, said second waist panel having a third direction of extensibility and said second thigh panel having a fourth direction of extensibility when a force is applied to said elastomeric second side panel, said fourth direction of extensibility being nonparallel to said third direction of extensibility.

2. The absorbent article of claim 1 wherein said waist panel and said thigh panel of each of said elastomeric first side panel and said elastomeric second side panel are a single component.

3. The absorbent article of claim 2 wherein each said single component elastomeric side panel is at least partially severed between said proximal edges and said distal edges.

4. The absorbent article of claim 1 wherein each said elastomeric side panel comprises a fold intermediate said waist panel and said thigh panel.

5. The absorbent article of claim 4 wherein said fold forms at least a portion of said distal edges of each said elastomeric side panel.

6. The absorbent article of claim 1 wherein at least a portion of each said elastomeric side panel is an extension of at least one component of said containment assembly.

7. The absorbent article of claim 1 additionally comprising a first proximal stiffening member joined to a portion of said elastomeric first side panel adjacent said first longitudinal edge of said containment assembly and a second proximal stiffening member joined to a portion of said elastomeric second side panel adjacent said second longitudinal edge of said containment assembly.

8. An absorbent article to be fitted to a wearer having a longitudinal centerline, a lateral centerline, a longitudinal direction parallel to the longitudinal centerline, a lateral direction parallel to the lateral centerline, a first waist region, a second waist region longitudinally opposed to said first waist region, a waist encirclable edge, a first leg encirclable edge, and a second leg encirclable edge, the absorbent article further comprising:

a) a containment assembly having a first longitudinal edge and a second longitudinal edge, a portion of said first longitudinal edge forming a portion of said first leg encirclable edge and a portion of said second longitudinal edge forming a portion of said second leg encirclable edge, a first end edge disposed in said first waist region and a second end edge disposed in said second waist region, said first end edge forming a portion of said waist encirclable edge and said second end edge forming a portion of said waist encirclable edge, said first longitudinal edge and said second longitudinal edge extending from said first end edge to said second end edge, said containment assembly further comprising a liquid pervious topsheet, a liquid impervious backsheet joined to said topsheet, and an absorbent core positioned between said topsheet and said backsheet;

b) a multiple component elastomeric first side panel disposed along said first longitudinal edge of said containment assembly in said first waist region and projecting laterally outwardly therefrom, said elastomeric first side panel comprising:

i) a first waist panel comprising a first waist panel member having a first direction of extensibility when a force is applied to said multiple component elastomeric first side panel, a first waist panel proximal edge adjacent said first longitudinal edge of said containment assembly, a first waist panel distal edge spaced laterally outwardly from said first waist panel proximal edge so as to be disposed laterally outboard of said first longitudinal edge of said containment assembly, said first waist panel proximal edge having a portion disposed adjacent said first end edge of said containment assembly, said first waist panel forming a portion of said waist encirclable edge of the absorbent article; and ii) a first thigh panel disposed longitudinally inboard of said first waist panel, said first thigh panel comprising a first thigh panel member having a second direction of extensibility when said force is applied to said multiple component elastomeric first side panel, said second direction of extensibility being nonparallel to said first direction of extensibility, a first thigh panel proximal edge adjacent said first longitudinal edge of said containment assembly, a first thigh panel distal edge spaced laterally outwardly from said first thigh panel proximal edge so as to be disposed laterally outboard of said first longitudinal edge of said containment assembly, a portion of said first thigh panel being overlapped with and joined to a portion of said first waist panel, said first thigh panel member being a distinct element from said first waist panel member and forming a portion of said first leg encirclable edge; and c) a multiple component elastomeric second side panel disposed along said second longitudinal edge of said containment assembly in said first waist region and projecting laterally outwardly therefrom, said elastomeric second side panel comprising:

i) a second waist panel comprising a second waist panel member having a third direction of extensibility when a force is applied to said multiple component elastomeric second side panel, a second waist panel proximal edge adjacent said second longitudinal edge of said containment assembly, a second waist panel distal edge spaced laterally outwardly from said second waist panel proximal edge so as to be disposed laterally outboard of said second longitudinal edge of said containment assembly, said second waist panel proximal edge having a portion disposed adjacent said first end edge of said containment assembly, said second waist panel forming a portion of said waist encirclable edge of the absorbent article; and ii) a second thigh panel disposed longitudinally inboard of said second waist panel, said second thigh panel comprising a second thigh panel member having a fourth direction of extensibility when said force is applied to said multiple component elastomeric second side panel, said fourth direction of extensibility being nonparallel to said third direction of extensibility, a second thigh panel proximal edge adjacent said second longitudinal edge of said containment assembly, a second thigh panel distal edge spaced laterally outwardly from said second thigh panel proximal edge so as to be disposed laterally outboard of said second longitudinal edge of said containment assembly a portion of said second thigh panel being overlapped with and joined to a portion of said second waist panel, said second thigh panel member being a distinct element from said second waist panel member and forming a portion of said second leg encirclable edge.

9. The absorbent article of claim 8 wherein said first direction of extensibility has a vector component oriented laterally outwardly that is greater than zero and a second vector component oriented towards said lateral centerline, said second direction of extensibility has a vector component oriented laterally outwardly that is greater than zero and a second vector component oriented away from said lateral centerline, said third direction of extensibility has a vector component oriented laterally outwardly that is greater than zero and a second vector component oriented towards said lateral centerline, and said fourth direction of extensibility has a vector component oriented laterally outwardly that is greater than zero and a second vector component oriented away from said lateral centerline.

10. The absorbent article of claim 8 wherein at least a portion of said first waist panel distal edge is joined to at least a portion of said first thigh panel distal edge and at least a portion of said second waist panel distal edge is joined to at least a portion of said second thigh panel distal edge.

11. The absorbent article of claim 8 additionally comprising a first proximal stiffening member joined to a portion of said elastomeric first side panel adjacent said first longitudinal edge of said containment assembly and a second proximal stiffening member joined to a portion of said elastomeric second side panel adjacent said second longitudinal edge of said containment assembly.

12. The absorbent article of claim 8 additionally comprising a pair fastening members joined to each said elastomeric side panel, one of said fastening members being disposed adjacent said waist panel distal edge and the other of said fastening members being disposed adjacent said thigh panel distal edge so as to allow the waist panel and the thigh panel to be fastened separately.

13. An absorbent article to be fitted to a wearer having a longitudinal centerline, a lateral centerline, a longitudinal direction parallel to the longitudinal centerline, a lateral direction parallel to the lateral centerline, a first waist region, a second waist region longitudinally opposed to said first waist region, a waist encirclable edge, a first leg encirclable edge, and a second leg encirclable edge, the absorbent article further comprising:

a) a containment assembly having a first longitudinal edge and a second longitudinal edge, a portion of said first longitudinal edge forming a portion of said first leg encirclable edge and a portion of said second longitudinal edge forming a portion of said second leg encirclable edge, a first end edge disposed in said first waist region and a second end edge disposed in said second waist region, said first end edge forming a portion of said waist encirclable edge and said second end edge forming a portion of said waist encirclable edge, said first longitudinal edge and said second longitudinal edge extending from said first end edge to said second end edge, said containment assembly further comprising a liquid pervious topsheet, a liquid impervious backsheet joined to said topsheet, and an absorbent core positioned between said topsheet and said backsheet;

b) a multiple component elastomeric first side panel disposed along said first longitudinal edge of said containment assembly in said first waist region and projecting laterally outwardly therefrom, said elastomeric first side panel comprising:

i) a first waist panel comprising a first waist panel member having a first direction of extensibility when a force is applied to said multiple component elastomeric first side panel, said first direction of extensibility having a vector component oriented laterally outwardly that is greater than zero and a second vector component oriented toward said lateral centerline, a first waist panel proximal edge adjacent said first longitudinal edge of said containment assembly, a first waist panel distal edge spaced laterally outwardly from said first waist panel proximal edge so as to be disposed laterally outboard of said first longitudinal edge of said containment assembly said first waist panel proximal edge having a portion disposed adjacent said first end edge of said containment assembly, a first waist panel first lateral edge running between said first waist panel proximal edge and said first waist panel distal edge, a first waist panel second lateral edge longitudinally opposed to said first waist panel first lateral edge, said first waist panel first lateral edge forming a part of said waist encirclable edge; and ii) a first thigh panel disposed longitudinally inboard of said first waist panel, said first thigh panel comprising a first thigh panel member having a second direction of extensibility when said force is applied to said multiple component elastomeric first side panel, said second direction of extensibility being nonparallel to said first direction of extensibility, said second direction of extensibility having a vector component oriented laterally outwardly that is greater than zero and a second vector component oriented away from said lateral centerline, a first thigh panel proximal edge adjacent said first longitudinal edge of said containment assembly, a portion of said first thigh panel being overlapped with and joined to a portion of said first waist panel, a first thigh panel distal edge laterally opposed to said first thigh panel proximal edge and being disposed laterally outboard of said first longitudinal edge of said containment assembly, a first thigh panel first lateral edge running between said first thigh panel proximal edge and the first thigh panel distal edge, a first thigh panel second lateral edge longitudinally opposed to said first thigh panel first lateral edge, said first thigh panel member being a distinct element from said first waist panel member, said first thigh panel second lateral edge forming part of said first leg encirclable edge;

c) a multiple component elastomeric second side panel disposed along said second longitudinal edge of said containment assembly in said first waist region and projecting laterally outwardly therefrom, said elastomeric second side panel comprising:

i) a second waist panel comprising a second waist panel member having a third direction of extensibility when a force is applied to said multiple component elastomeric second side panel, said third direction of extensibility having a vector component oriented laterally outwardly that is greater than zero and a second vector component oriented toward said lateral centerline, a second waist panel proximal edge adjacent said second longitudinal edge of said containment assembly, a second waist panel distal edge spaced laterally outwardly from said second waist panel proximal edge so as to be disposed laterally outboard of said second longitudinal edge of said containment assembly, said second proximal edge having a portion disposed adjacent said first end edge of said containment assembly, a second waist panel first lateral edge running between said second waist panel proximal edge and said second waist panel distal edge, a second waist panel second lateral edge longitudinally opposed to said second waist panel first lateral edge, said second waist panel first lateral edge forming a part of said waist encirclable edge; and ii) a second thigh panel disposed longitudinally inboard of said second waist panel, said second thigh panel comprising a second thigh panel member having a fourth direction of extensibility when said force is applied to said multiple component elastomeric second side panel, said fourth direction of extensibility being nonparallel to said third direction of extensibility, said fourth direction of extensibility having a vector component oriented laterally outwardly that is greater than zero and a second vector component oriented away from said lateral centerline, a second thigh panel proximal edge adjacent said second longitudinal edge of said containment assembly, a portion of said second thigh panel being overlapped with and joined to a portion of said second waist panel, a second thigh panel distal edge laterally opposed to said second thigh panel proximal edge and being disposed laterally outboard of said second longitudinal edge of said containment assembly, a second thigh panel first lateral edge running between said second thigh panel proximal edge and said second thigh panel distal edge, a second thigh panel second lateral edge longitudinally opposed to said second thigh panel first lateral edge, said second thigh panel member being a distinct element from said second waist panel member, said second thigh panel second lateral edge forming part of said second leg encirclable edge; and d) a first fastening member disposed adjacent said first waist panel distal edge and said first thigh panel distal edge and joined to both said first waist panel and said first thigh panel, and a second fastening member disposed adjacent said second waist panel distal edge and said second thigh panel distal edge and joined to both said second waist panel and said second thigh panel.

14. The absorbent article of claim 13 wherein said second vector component of said first direction of extensibility is greater than zero, said second vector component of said second direction of extensibility is greater than zero, said second vector component of said third direction of extensibility is greater than zero, and said second vector component of said fourth direction of extensibility is greater than zero.

15. The absorbent article of claim 14 additionally comprising a first proximal stiffening member joined to a portion of said multiple component elastomeric first side panel adjacent said first longitudinal edge of said containment assembly and a second proximal stiffening member joined to a portion of said multiple component elastomeric second side panel adjacent said second longitudinal edge of said containment assembly.

16. The absorbent article of claim 15 wherein said first fastening member has a primary centerline forming an angle with the lateral direction.

* * * * *